(12) United States Patent
Ziegler

(10) Patent No.: US 6,524,106 B1
(45) Date of Patent: Feb. 25, 2003

(54) FASTENER FOR ATTACHING TO A DENTAL FIXTURE AND RELATED METHODS

(75) Inventor: Andrew Ziegler, Arlington, MA (US)

(73) Assignee: Atlantis Components, Inc., Cambridge, MA (US)

( * ) Notice: Subject to any disclaimer, the term of this patent is extended or adjusted under 35 U.S.C. 154(b) by 84 days.

(21) Appl. No.: 09/662,700

(22) Filed: Sep. 15, 2000

Related U.S. Application Data

(63) Continuation-in-part of application No. 09/184,730, filed on Nov. 2, 1998, now Pat. No. 6,149,433, which is a continuation-in-part of application No. 08/851,836, filed on May 5, 1997, now Pat. No. 5,829,981.

(51) Int. Cl.⁷ .................................................. A61C 9/00
(52) U.S. Cl. ........................................ 433/214; 433/213
(58) Field of Search ................................ 433/172, 173, 433/174, 213, 214

(56) References Cited

U.S. PATENT DOCUMENTS

| | | |
|---|---|---|
| 4,681,542 A | 7/1987 | Baum |
| 4,758,161 A | 7/1988 | Niznick |
| 4,955,811 A | 9/1990 | Lazzara et al. |
| 4,988,297 A | 1/1991 | Lazzara et al. |
| 5,052,929 A | 10/1991 | Seal |
| 5,104,318 A | 4/1992 | Piche et al. ................. 433/174 |
| 5,106,300 A | 4/1992 | Voitik ......................... 433/173 |
| 5,125,839 A | 6/1992 | Ingber et al. ............... 433/169 |
| 5,125,841 A | 6/1992 | Carlsson et al. ........... 433/213 |
| 5,193,999 A | 3/1993 | Staubli ........................ 433/72 |
| 5,213,502 A | 5/1993 | Daftary ...................... 433/172 |
| 5,297,963 A | 3/1994 | Dafatry ...................... 433/172 |
| 5,334,024 A | 8/1994 | Niznick ...................... 433/173 |
| 5,338,196 A | 8/1994 | Beaty et al. ................ 433/172 |
| 5,362,235 A | 11/1994 | Daftary ...................... 433/172 |
| 5,362,237 A | 11/1994 | Chalifoux ................... 433/220 |
| 5,417,568 A | 5/1995 | Giglio ........................ 433/173 |
| 5,419,702 A | 5/1995 | Beaty et al. ................ 433/214 |
| 5,447,435 A | 9/1995 | Brodbeck ................... 433/173 |

(List continued on next page.)

FOREIGN PATENT DOCUMENTS

| | | |
|---|---|---|
| WO | WO 96/34576 | 11/1996 |
| WO | WO 97/37610 | 10/1997 |
| WO | WO 99/02102 | 1/1999 |

OTHER PUBLICATIONS

Wheeler, *Dental Anatomy, Physiology and Occlusion*, W.B. Saunders Co., Philadelphia, PA, pp. 3–23 (Fifth Edition, 1974).

*3i Restorative Catalog, Restorative Leadership Through Precision and Innovation*, West Palm Beach, FL, 12 pages, 2000.

Steri–Oss, Product Catalog, Yorba Linda, CA, pp. 20, 24, 28, 32, 39, 45, Jul. 1998.

*Replace™Implant System*, Product Catalog, Steri–Oss, Yorba Linda, CA, pp. 8, 16, 26, 36, Jan. 1999.

*Nobel biocare*, U.S. Product Catalog, 5ᵗʰ ed., Yorba Linda, CA, Brånemark System, pp. 38, 41, 43, 47, 49, 52, 54, 56, 58, 61, 63, 65, 67, 70, date unknown.

"Stage 1 Indexing Kit: Three Easy Steps", *Atlantis Corporation Components, Inc.*, Cambridge, MA, 2 pages, Jun. 1, 2000.

"Stage 1 Index Kit: Three Easy Steps", *Atlantis Components, Inc.*, Cambridge, MA, 1 page, Dec. 1, 1999.

*Primary Examiner*—Ralph A. Lewis
(74) *Attorney, Agent, or Firm*—Testa, Hurwitz & Thibeault, LLP

(57) ABSTRACT

Fasteners having two or more threaded portions seat impression copings which are used to take an impression of local dentition and related methods. The threaded portions are of a different size.

16 Claims, 16 Drawing Sheets

U.S. PATENT DOCUMENTS

| | | |
|---|---|---|
| 5,476,383 A | 12/1995 | Beaty et al. ................. 433/214 |
| 5,492,471 A | 2/1996 | Singer ........................ 433/172 |
| D370,978 S | 6/1996 | Broberg et al. |
| 5,527,182 A | 6/1996 | Willoughby ................. 433/172 |
| 5,571,015 A | 11/1996 | Siegmund ................... 433/173 |
| 5,658,147 A | 8/1997 | Phimmasone ............... 433/213 |
| 5,662,476 A | 9/1997 | Ingber et al. ................ 433/213 |
| 5,674,069 A | 10/1997 | Osorio |
| 5,674,073 A | 10/1997 | Ingber et al. ................ 433/213 |
| 5,685,715 A | 11/1997 | Beaty et al. ................. 433/173 |
| 5,688,123 A | 11/1997 | Meiers et al. ............... 433/173 |
| 5,829,981 A | 11/1998 | Ziegler ........................ 433/214 |
| 5,938,443 A | 8/1999 | Lazzara et al. ............. 433/173 |
| 5,989,029 A | 11/1999 | Osorio et al. |
| 6,149,433 A | 11/2000 | Ziegler et al. ............... 433/214 |

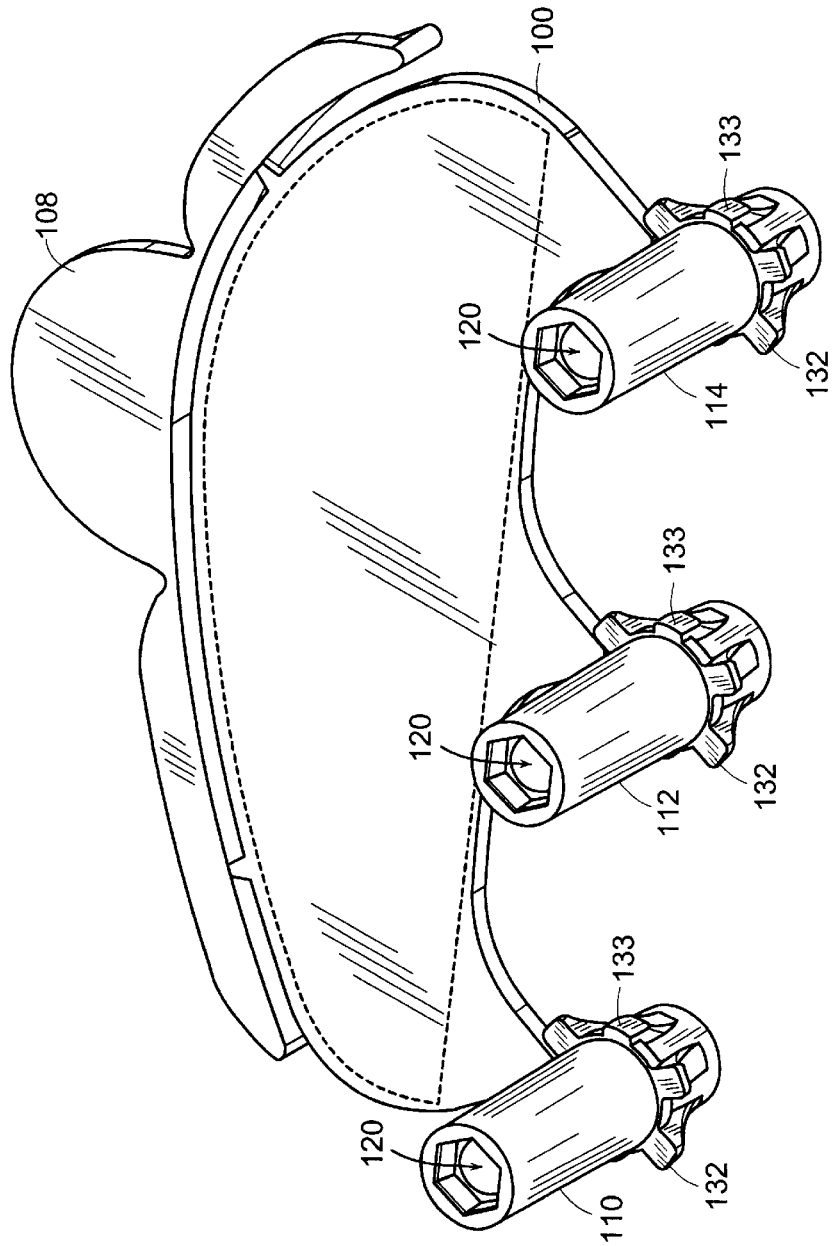
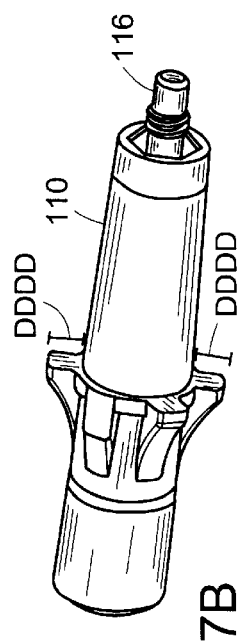
FIG. 7A
FIG. 7B

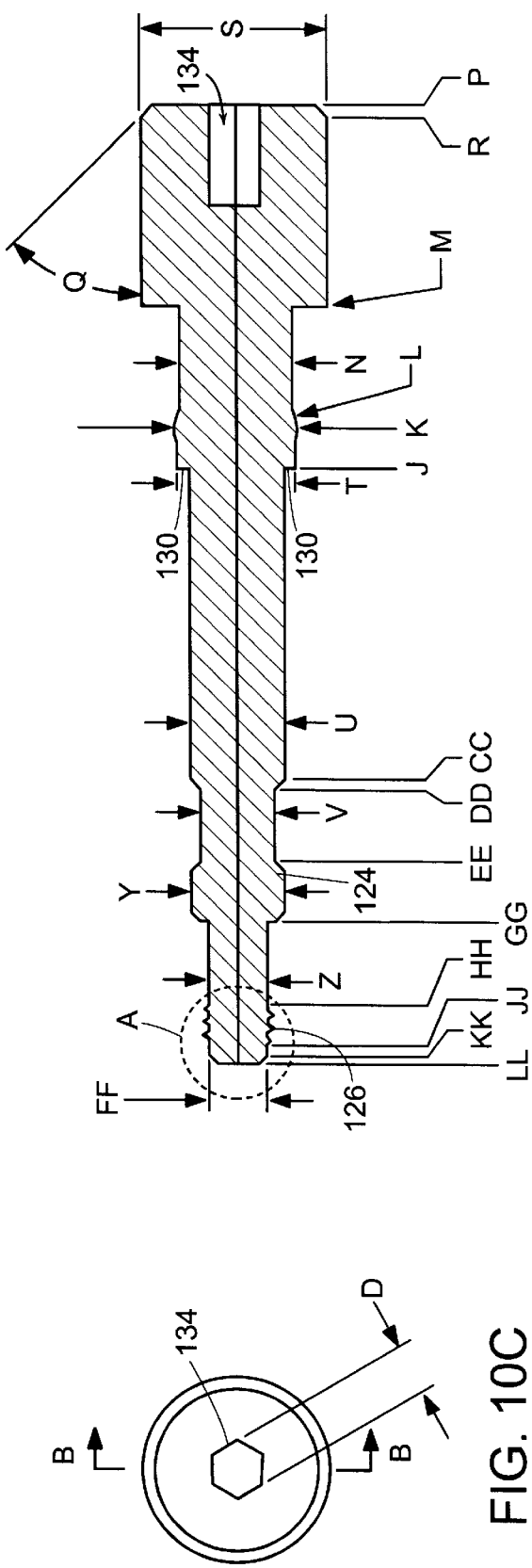
FIG. 10D
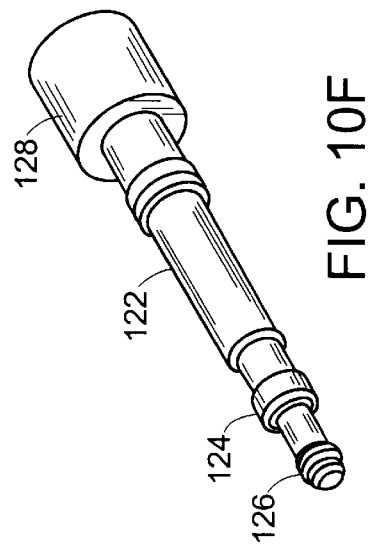
FIG. 10F
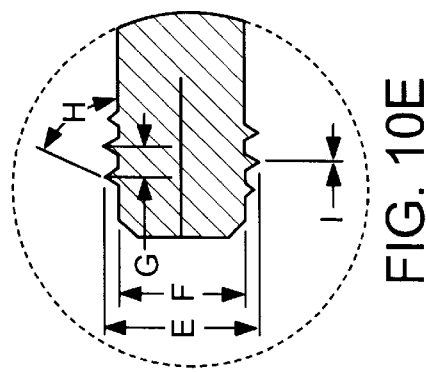
FIG. 10E
FIG. 10C

US 6,524,106 B1

FASTENER FOR ATTACHING TO A DENTAL FIXTURE AND RELATED METHODS

CROSS-REFERENCE TO RELATED APPLICATIONS

This application is a continuation-in-part of co-pending U.S. Ser. No. 09/184,730 (U.S. Pat. No. 6,149,433), filed on Nov. 2, 1998, which is a continuation-in-part of U.S. Ser. No. 08/851,836 (U.S. Pat. No. 5,829,981), filed May 5, 1997, the disclosures of which are incorporated herein by reference. This application also is related to the U.S. Patent Application entitled "Impression Coping Platform and Related Methods," filed on even date herewith, U.S. Ser. No. 09/663,728, (pending), the entire disclosure of which is incorporated herein by reference.

FIELD OF THE INVENTION

The invention relates to the field of anatomical dental implant systems. More particularly, the invention relates to the field of impression copings for implant restorations.

BACKGROUND OF THE INVENTION

Dental restorative systems seek to provide cosmetic and functional replacements for missing teeth. Typically, methods for tooth replacement involve placement of an anchor, called a dental fixture, in the patient's jaw. The dental fixture is inserted into a hole drilled into the jaw. It provides a receptacle for the replacement tooth. Prior to replacement, however, an impression of the local dentition must be taken. The impression should preserve features of the dentition, including the position and alignment of the site for tooth replacement. An integral feature of this process is the use of an impression coping device, which serves to orient and preserve the impression of the local dentition. This allows a technician to form a replacement tooth that matches the contour and orientation of the natural teeth. The impression coping device typically is placed into the bore of the dental fixture, described above. In some dental restorative systems, a screw or bolt is used to anchor the impression coping device in the dental fixture. Once the impression coping device is screwed into the dental fixture, an impression of the local dentition can be taken.

Proper orientation of a replacement tooth is important both cosmetically and functionally. The impression coping device aids in this process by providing a substrate for an impression of the area in which tooth replacement will occur. The impression is formed around the impression coping device in a patient's mouth. The impression coping device and the attached impression are then removed from the patient's mouth, and are used as a basis for construction and orientation of a replacement tooth by a dental technician.

Typically, a screw assembly is used to secure an impression coping device to an implanted dental fixture. A dental fixture, therefore, generally consists of a central bore with screw threads for receiving a screw. The exposed surface (i.e., the surface of the fixture protruding from bone) of an implanted dental fixture typically consists of a hexagonal or round interface for defining the orientation of attachment of a tooth analog. An impression coping device is attached to the dental fixture by a screw that threads through the coping and into a central bore of the fixture. The screw mates with threads in the fixture in order to secure the impression coping. An impression of the dentition surrounding the tooth to be replaced is then taken. The impression then is removed from the mouth and used to fabricate a tooth analog, as indicated above.

In the art, in order to obtain a proper fit of the tooth analog, it is desirable to maintain rotational alignment between the implanted fixture and the patient's natural dentition. This requires that the impression coping device engage the implanted fixture in a non-rotational manner. Some screw mechanisms used to secure impression copings tend to interfere with the rotational alignment of the impression.

Difficulties in handling and properly installing screws or bolts to secure coping devices have lead to improvements, such as an interlocking coping device comprising a screw that is non-removably inserted through the central bore, thus allowing insertion of the coping device and the screw in one step.

Some of the major manufacturers in the dental restorative industry produce dental fixtures. In some instances, these dental fixtures have a male hexagonal head on the end of the dental fixture that protrudes from the patient's jaw. Manufacturers typically will produce a variety of dental fixtures having differentially-sized male hexagonal heads (often two or three sizes of male hexagonal head). The male hexagonal head of the dental fixtures mates with a female hexagonal mating surface on an impression coping device. A dental professional chooses a dental fixture appropriate for a particular application and uses an impression coping having an appropriately-sized, female hexagonal mating surface to mate with the dental fixture. Moreover, depending on the manufacturer, different dental fixtures may have a unique threaded bore that accepts a screw that interacts with a dental impression coping.

SUMMARY OF THE INVENTION

The invention provides platforms for holding and selecting impression copings during various dental procedures. Accordingly, the invention allows rapid and accurate selection of appropriate impression copings during a dental procedure, thus reducing trial and error selection of impression copings and the necessity to preselect impression copings prior to taking an impression. The platform also allows a dental professional to conveniently select and sterilize an amount of impression copings prior to undertaking the procedure. Often, prior to undertaking a dental procedure, the dental professional does not know which size dental fixture(s) will be used. As such, the dental professional must ensure that a sufficient number of impression copings are prepared prior to undertaking the procedure, and often must guess at the correct sizes that will be necessary. The invention provides platforms that hold a selection of impression copings that are complementary to available dental fixtures. A single platform according to the invention may be used for a single procedure, thus reducing the necessity for multiple sterilizations and preselection of multiple impression coping types. Accordingly, in some embodiments of the invention, the dental professional need only choose and sterilize one platform for each dental fixture that will be used during the procedure (or that is already implanted in the patient's jaw if the dental fixture implantation and the impression-taking are not occurring during the same procedure). This convenience is especially apparent when more than one dental fixture is involved.

The present invention also provides fasteners, such as, but without limitation, screws, for use with impression copings. To the extent that an impression coping is held in place or is supplementally seated with a fasteners, fasteners, such as, but without limitation, screws, according to the invention have at least two separate threaded areas to accommodate variously-sized dental fixtures. As such, the dental professional can quickly mate and secure an impression coping to various dental fixtures having differently sized threaded bores with a screw that engages with the threaded bores, without having to choose a correctly sized screw. Moreover, only a single screw need be supplied, rather than multiple screws, to provide a fastener for various dental fixture sizes.

The invention is not limited to dental fixtures having a male hexagonal head, but this example provides a useful paradigm. For example, some other dental fixture manufacturers in the industry produce fixtures that utilize other types of interfaces between the fixture and the impression coping. For example, the fixture can have a female hexagonal mating surface and the impression coping can have a male hexagonal head, or, for example, the dental fixture can contain teeth that mesh with a complementary structure on the impression coping. These dental fixtures utilizing alternative mating options also can be produced in various sizes such that variously-sized impression copings and/or fasteners are necessary. Thus, in any situation in which variously-sized dental fixtures are sold, variously-sized impression coping devices are necessary for attaching to the variously-sized fixtures. Furthermore, variously-sized threaded screws are necessary to attach to the variously-sized dental fixtures when such fasteners are necessary.

In a preferred embodiment of the invention, a fastener for use with an impression coping includes a first threaded portion and a second threaded portion. The first threaded portion is along an axis and has a first major diameter, and the second threaded portion is along the axis and has a second, different major diameter. The first threaded portion and the second threaded portion are separated by an unthreaded portion.

In some embodiments, a fastener of the invention includes a third threaded portion that is along the axis and is separated from the second threaded portion by a second unthreaded portion. Also in a preferred embodiment, a fastener of the invention includes a first major diameter that is smaller than a second major diameter. In certain embodiments, the first threaded portion is located closer to a distal end of the fastener than the second threaded portion. A preferred fastener according to the invention includes a bulge that is concentric with the axis of the fastener at a location that is closer to a proximal end of the fastener than is the second threaded portion. A fastener of the invention also can include a shoulder that is concentric with the fastener axis at a location that is closer to the distal end of the fastener than is the bulge. In some embodiments, the invention provides a fastener including a first threaded portion and a second threaded portion, at least one of which has a major diameter of about 1 millimeter to about 3 millimeters. Also, in some embodiments, the first threaded portion has a major diameter of between about 1 millimeter to about 2 millimeters, and the second threaded portion has a different major diameter of between about 1.5 millimeter to about 3 millimeters. In embodiments with a third threaded portion, the third threaded portion may have a major diameter of about 1 millimeter to about 3 millimeters. Fasteners according to the invention are not limited to these dimensions. In some preferred embodiments, at least one of the threaded portions can engage with a dental fixture, and/or an impression coping can be seated on the dental fixture.

Another aspect of the invention provides methods for seating an impression coping. Methods of the invention include the steps of providing a fastener, inserting the fastener through an impression coping; and, securing the fastener to a dental fixture. Fasteners for use in methods of the invention preferably are selected from those described above as well as below.

In another aspect of the invention, a dental impression kit includes an impression coping and a fastener for inserting through the impression coping to seat the impression coping on a dental fixture. In certain embodiments, the fastener includes a first threaded portion and a second threaded portion. The first threaded portion is along an axis and has a first major diameter. The second threaded portion is along the same axis and has a second, different major diameter. The first threaded portion and the second threaded portion are separated by an unthreaded portion. In some embodiments, the impression coping is of a length that exposes a selected portion of the fastener when the fastener is inserted though the impression coping. In some preferred embodiments, the fastener can include a bulge that is concentric with the axis and has an outer diameter that is larger than an inner diameter of a lip located within the impression coping. The fastener and impression coping also can interact with a radial interference interaction.

In another aspect of the invention, a dental impression tool support kit includes a platform and at least one impression coping attached to the platform at a frangible connection. In certain embodiments, the kit includes a reinforcing member attached to the platform at a frangible connection. In some embodiments, from about one to about seven impression copings are attached to a single platform. Any of the impression copings may include a head for releasable mating with a dental fixture, and the heads may be differently-sized for mating with differently-sized dental fixtures. At least one of the impression copings may include a female, hexagonal structure, and a platform may include a male, hexagonal structure for mating with the impression coping having the female, hexagonal structure.

In another aspect of the invention, a dental impression kit includes a platform, at least one impression coping attached to the platform, and a fastener for inserting through the impression coping. In certain embodiments, the kit can include a reinforcing member attached to the platform and/or can include from about one to about seven impression copings attached to the platform. In some embodiments, the fastener can include a first threaded portion and a second threaded portion. The first threaded portion is along an axis and has a first major diameter. The second threaded portion is along the axis and has a second, different major diameter. The first threaded portion and the second threaded portion are separated by an unthreaded portion.

In another aspect of the invention, a member for supporting a dental impression includes a first arcuate portion having a first profile, a second arcuate portion disposed adjacent the first arcuate portion and having a second, different profile, and a third portion protruding from the member at an intersection of the first and second portions. A section of the member can be selectively detachable at a frangible connection. In another aspect of the invention, a method for reinforcing a dental impression includes providing a member as described immediately above, or below, and inserting the member into an impression material.

The invention will be understood further upon consideration of the following drawings, description and claims.

DESCRIPTION OF THE DRAWINGS

The invention is more particularly described in the following detailed description, drawings, and claims. In the drawings, like reference characters generally refer to the same parts throughout the different views. Also, the drawings are not necessarily to scale, emphasis instead generally being placed upon illustrating principles of the invention.

FIG. 7A depicts the platform of FIG. 6 attached to three impression coping devices.

FIG. 7B depicts a screw inserted through one of the impression coping devices of FIG. 7A.

FIG. 10C depicts a top view of the screw of FIG. 10A.

FIG. 10D depicts a sectioned, stylized profile view of the screw of FIG. 10A taken along line B—B of FIG. 10C.

FIG. 10E depicts a detail view of a thread profile taken in circle A of FIG. 10D.

FIG. 10F depicts a highly stylized view of the screw of FIG. 10A.

DETAILED DESCRIPTION OF THE INVENTION

The present invention provides platforms that hold impression copings. For example, a platform can hold variously-sized impression copings. These copings can take many forms, and some of the embodiments of these copings are disclosed herein. However, other copings known in the art also can be attached to a platform according to the invention. Platforms according to the invention allow a dental professional to conveniently and quickly choose and prepare an appropriately sized impression coping for a dental procedure.

The present invention also provides fasteners, such as, but without limitation, screws, for use with impression copings, to the extent that a particular impression coping is seated, or is seated in a supplementary manner, with the aid of a fastener, such as, but without limitation, a screw. Such screws have at least two separate threaded areas to accommodate variously-sized threaded bores in dental fixtures. For example, a particular manufacturer of dental fixtures might produce several different sizes of fixture, each with a differently sized threaded bore for accepting a screw. A screw with several differently sized threaded portions can engage with any of these fixtures. As such, the dental professional can quickly seat the impression coping on various dental fixtures having differently sized bores when the dental professional uses embodiments of impression copings and/or dental fixtures for which the use of a screw is recommended. Moreover, only a single screw need be supplied, rather than multiple screws, to provide a fastener for various dental fixture bore sizes. Some impression coping device embodiments are disclosed herein while others are known in the art.

Certain impression copings of the invention releasably attach to a dental fixture by a friction-fit mating, a snap-fit mating, a threaded mating, or other mating means. A fastener (e.g., a screw) can be used for seating the coping device properly. As a result of the friction-fit mating between the impression coping device and the dental implant, the device may be inserted and removed without disturbing its rotational alignment with respect to the existing dentition. This makes it quicker and easier for a practitioner to make an impression of the local dentition that is useful for construction of a replacement tooth that has the same geometric architecture as the surrounding area into which the replacement tooth is placed. Thus, it is clear that an impression coping device of the invention may take many forms, depending, inter alia, on the dental fixture with which it mates, the location into which a replacement tooth is placed, the surface area necessary or desirable for anchoring an impression, and other factors known to the skilled person.

Figure 1A:
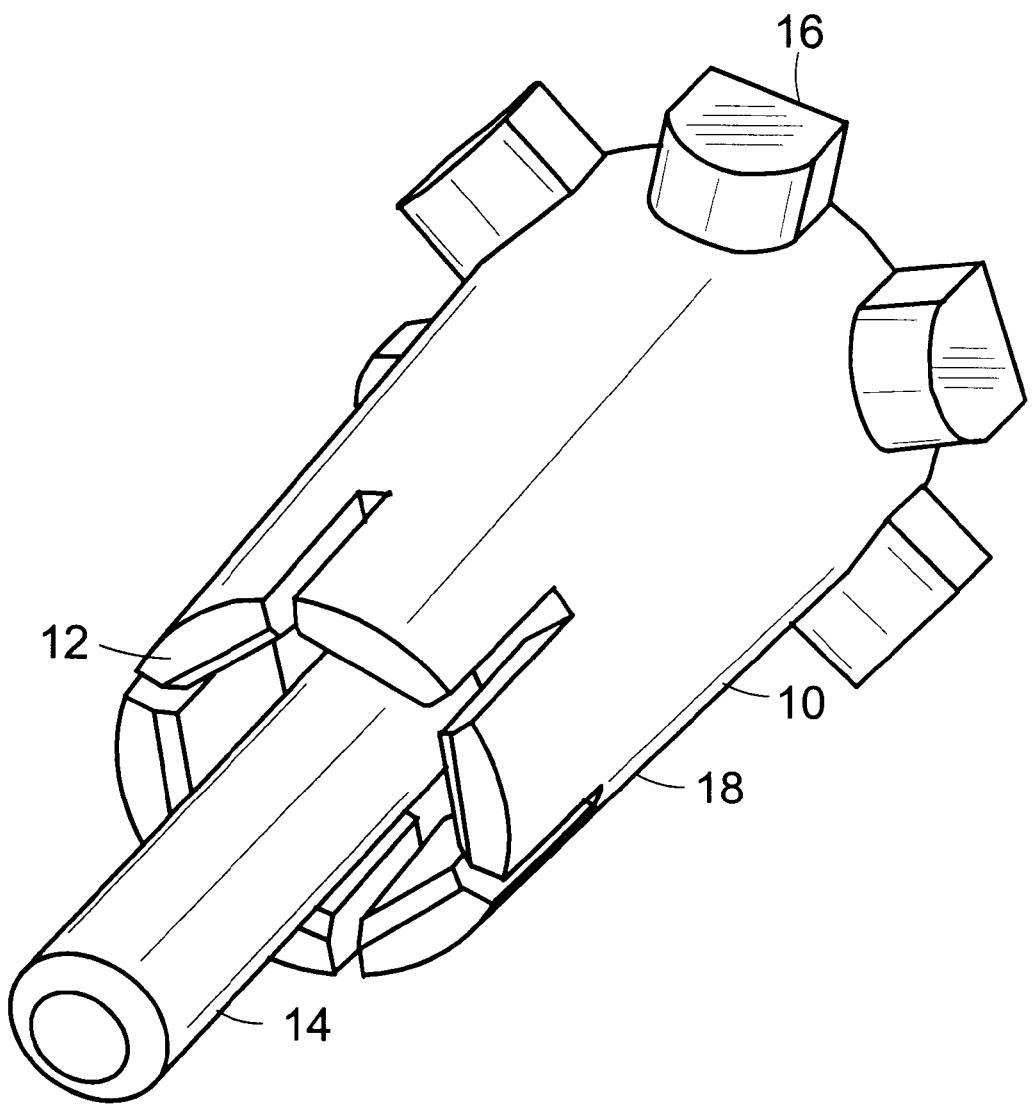
FIG. 1A illustrates a bottom view of an impression coping device of the invention.
Figure 1B:
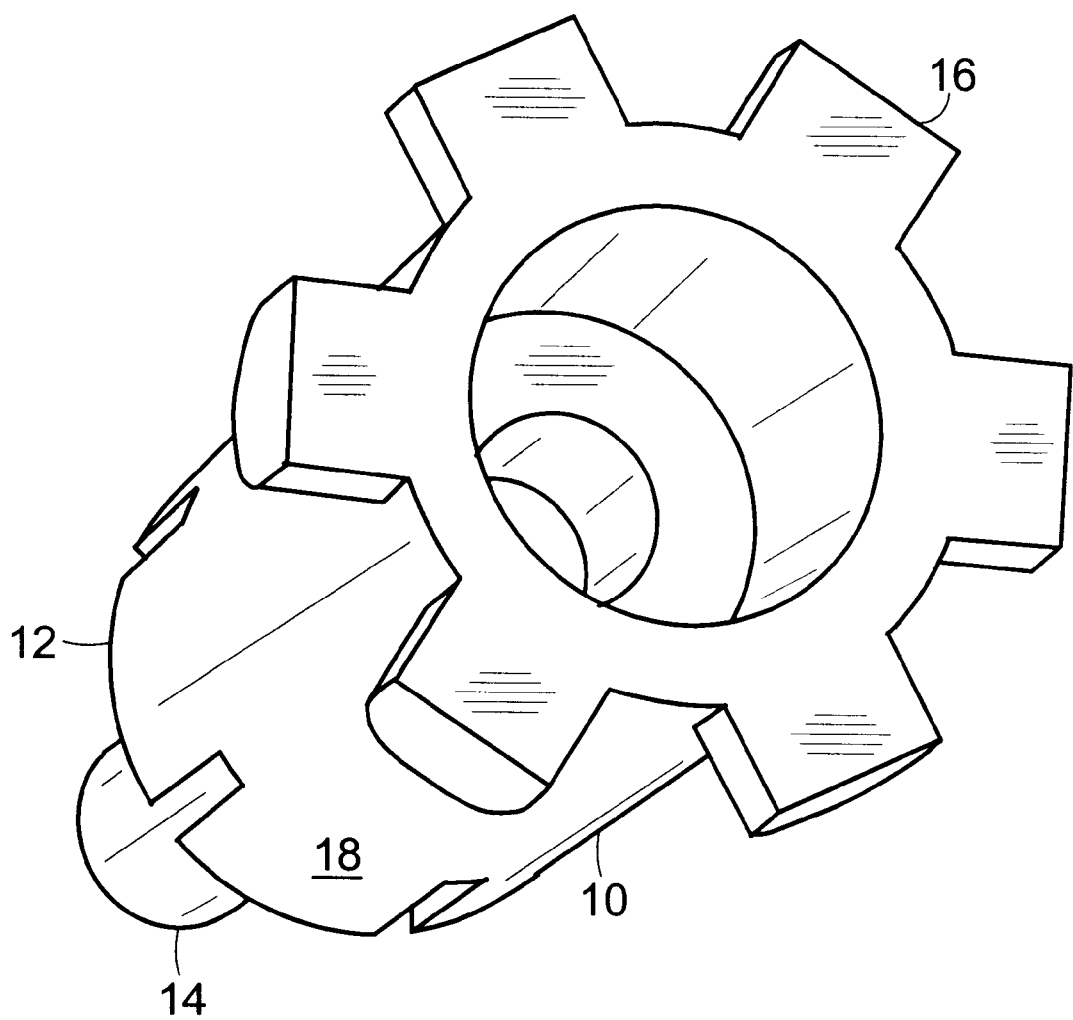
FIG. 1B illustrates a top view of an impression coping device of the invention.

One embodiment of an impression coping of the invention comprises a head having a first end that releasably attaches to a dental fixture. The first end is castellated, as shown in FIGS. 1A and 1B. The castellated end comprises a plurality of axially extending, radially resilient fingers that deflect as they are friction fitted over a mating surface of a dental fixture. Further, the castellated end comprises an inner surface which corresponds to mating detail on the surface of a dental fixture. Expansion of the fingers causes the castellated end to radially friction fit onto the reciprocal mating surface of the fixture.

The radial friction fit between corresponding mating surfaces of the impression coping device and the dental fixture allows releasable attachment of the device to the dental fixture with or without the use of screws. Thus, the orientation and alignment of an impression of the local dentition are preserved. In certain embodiments, an impression coping device for establishing the relative position of a dental implant has spaced-apart castellated fingers at the point of attachment to a dental fixture. The spaced-apart fingers allow visual inspection of the attached coping device.

Figure 3:
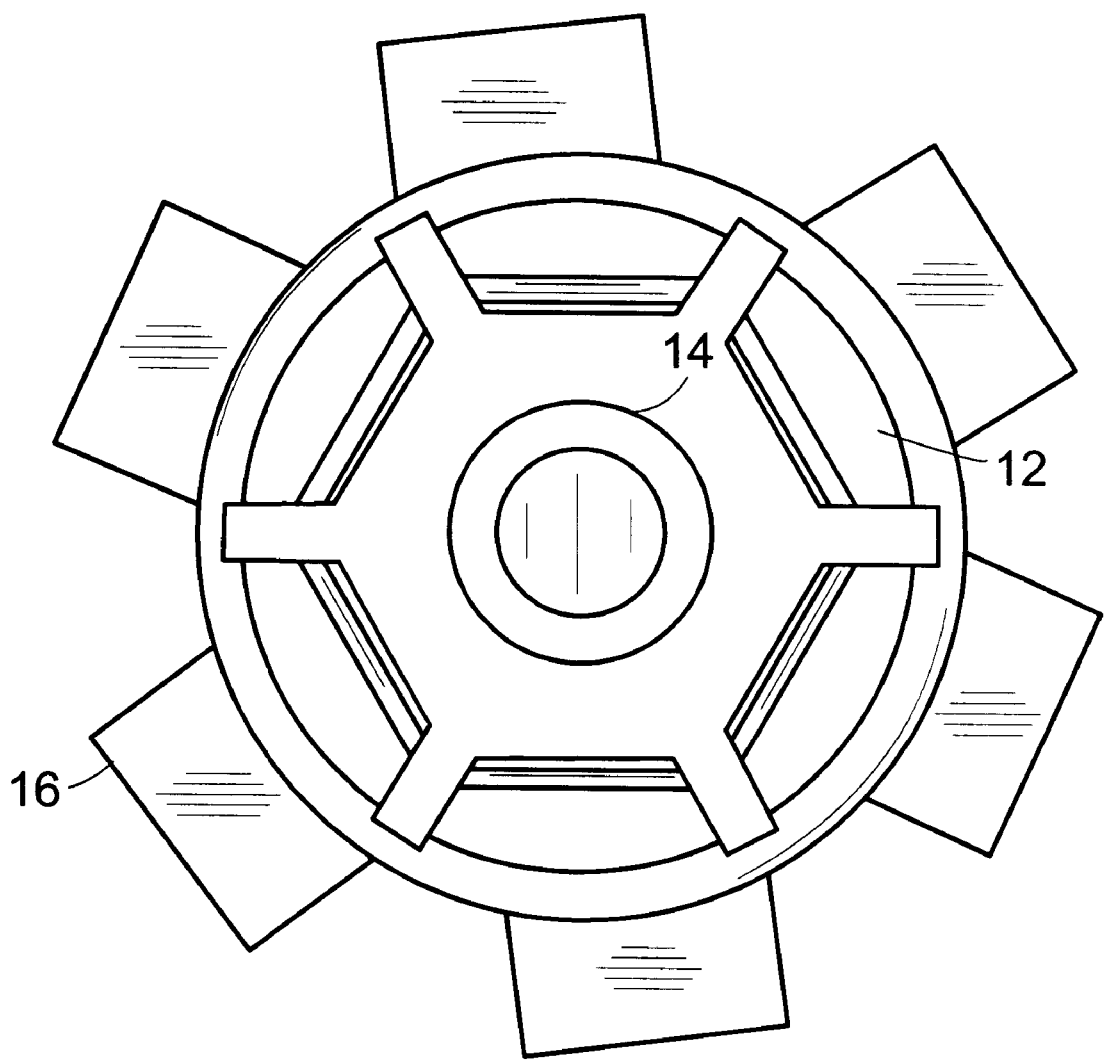
FIG. 3 is a bottom view of an impression coping device of the invention.

Now referring to FIG. 1A, one embodiment of an impression coping device has a first end comprising a head 10 that is substantially frusto-conical or cylindrical in shape. The head has a castellated end 18, which has a hexagonal inner surface for mating with a corresponding surface of a dental fixture (not shown). The castellated end of the head comprises axially-extending, radially-resilient fingers 12, which form a flexible hexagonal inner surface for providing a radial friction fit with a corresponding dental fixture mating surface. FIG. 3 shows a hexagonal mating detail of an impression coping device of the invention. Like reference numerals in FIGS. 1B and 3 refer to like elements in FIG. 1A. The hexagonal mating detail makes reciprocal contact with a corresponding mating detail on a dental fixture in order to hold the impression coping device in place.

Figure 2B:
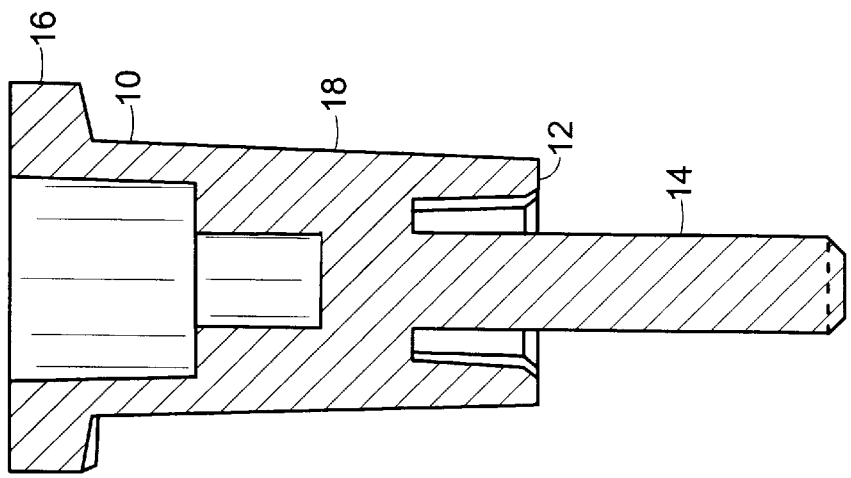
FIG. 2B is a cross-sectional view of the device shown in FIG. 2A.
Figure 2A:
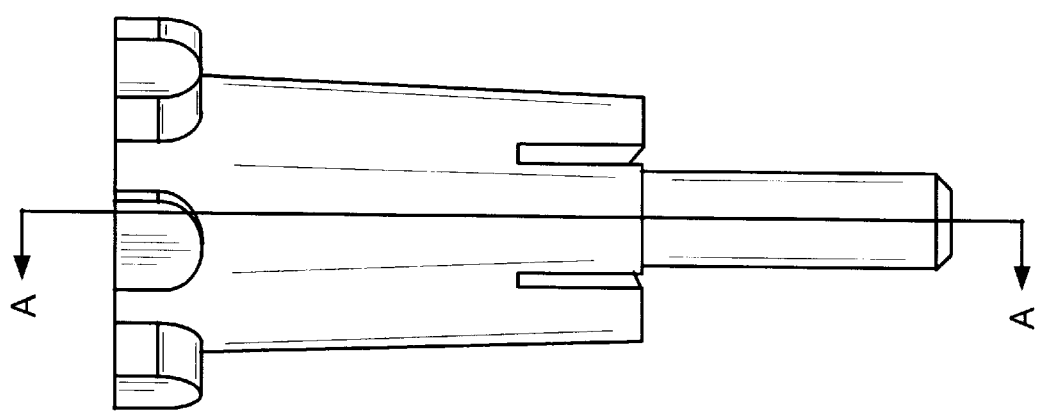
FIG. 2A is a side view of an impression coping device of the invention.

As shown in FIG. 1A, attached to the first end is a guide stem 14. The guide stem is fitted for mating into the central bore of a dental fixture. The guide stem may extend into the recessed pocket of the head, as shown in FIGS. 1A and 2B, or it may terminate on the flat hexagonal surface created by the castellated end. The guide stem also can extend through the entire device, and can be separable from the device. The guide stem can be threaded or unthreaded.

Figure 4:
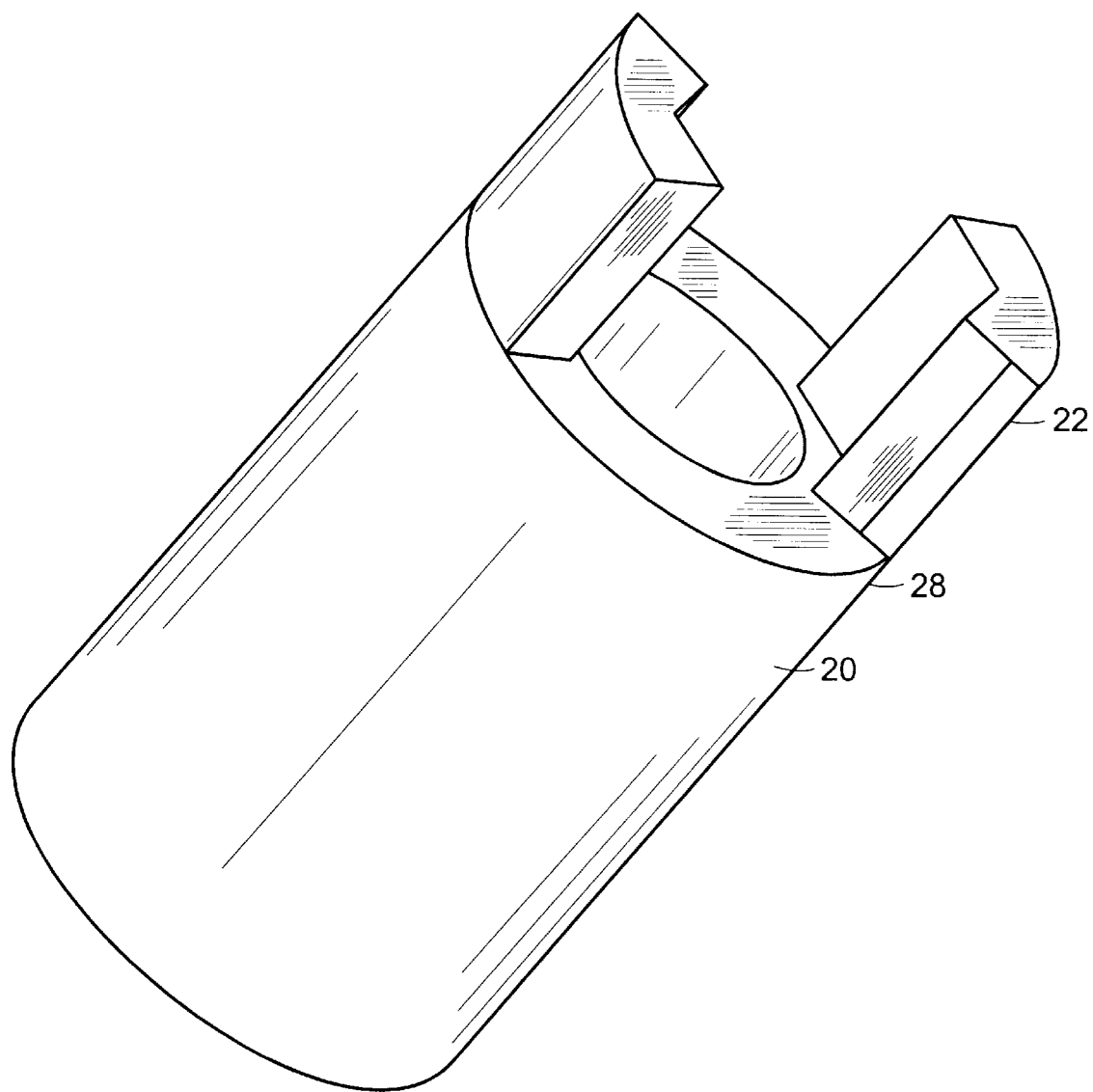
FIG. 4 is a stylized side view of an impression coping device of the invention.
Figure 5:
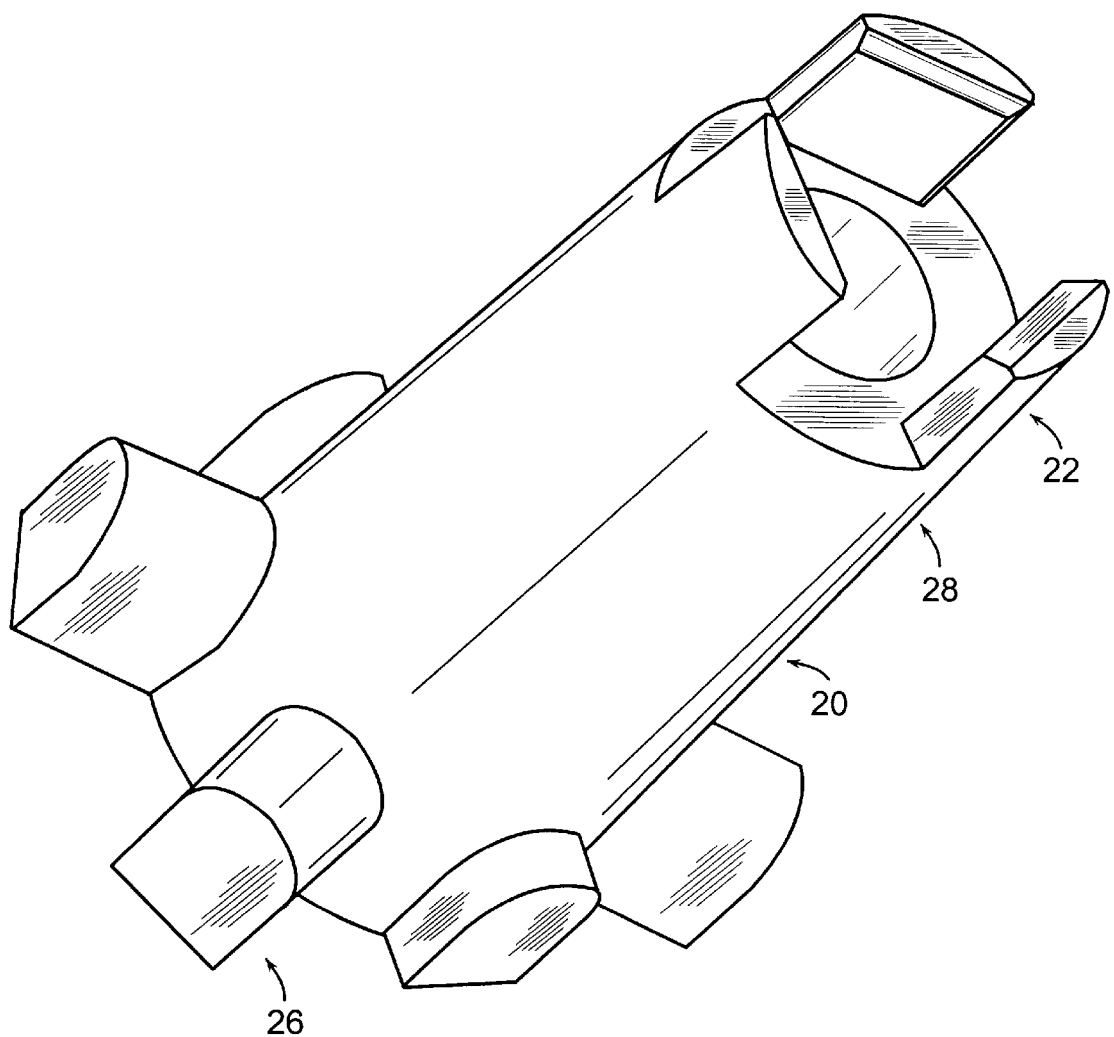
FIG. 5 is a side view of an impression coping device of the invention.

Another embodiment of an impression coping device of the invention is shown in FIG. 5. The device has a first end comprising a head 20 that is substantially frusto-conical or cylindrical in shape. The head has a castellated end 28, which has an inner surface that is complementary to a hexagon for mating with a corresponding surface of a dental fixture (not shown). The castellated end of the head comprises three spaced-apart axially-extending, radially resilient fingers 22, which form a flexible inner surface that is complementary to a hexagon for providing a radial friction fit with a corresponding dental fixture mating surface. FIG. 4 shows an alternative embodiment of the impression coping device with two axially-extending, radially resilient fingers. Like reference numerals in FIGS. 4 and 5 refer to like elements. The spacing between fingers allows visual inspection of the coping device as attached to the fixture. The ability to visually inspect the attached device/fixture ensures that a proper mating has been achieved between the coping and the fixture (i.e., that the mating has retained proper geometry for taking an accurate impression). The spacing between fingers can be any distance that allows for visual inspection of the coping device as attached to the fixture. A preferred spacing of the fingers is between 0.5 mm and 3 mm. A particularly preferred spacing is between 1 mm and 2 mm.

A second end of the head comprises one or more radially arranged flanges 16. These are arranged to provide an anchor for impression molding material applied to the dentition in the vicinity of the replacement site. The flanges provide surface area for attachment of the molding material, thereby facilitating its removal from the mouth upon curing.

Typically, an impression coping device of the invention is constructed from a biologically compatible material. Biologically compatible materials include, but are not limited to, polycarbonate, high-impact polystyrene, and polyetherimide. An impression coping device of the invention can be made by well-known processes. Such processes include, for example, injection-molding or stereolithography.

An impression coping device of the invention is used as an aid in performing a single or multiple tooth restoration. Generally, a study cast of a patient's existing teeth is first made. Then, a dental fixture, such as that manufactured by Life Core, is implanted in a bore hole made in a patient's jaw at the site of desired tooth replacement. The implant site is surgically prepared by drilling into the jawbone after the gingival tissue surrounding the point of insertion of the implant has been retracted.

One type of dental fixture comprises a male hexagonal interface at its exposed end and is therefore compatible with certain impression coping devices of the invention having a female hexagonal interface on the castellated end of the head. As described above, the dental fixture also contains a hollow bore, which is open from the exposed end of the fixture and extends into the fixture. The hollow portion of the implant fixture may or may not have inner screw threads.

A coping device of the invention can be attached to the implanted dental fixture using a radial friction fit that is formed between the castellated end of the impression coping device and the corresponding hexagonal mating end of the dental fixture. The fingers of the castellated end expand as the device is forced over the male hexagonal interface of the fixture. The radial friction fit between the two hexagonal interfaces prevents the coping device from rotating on the fixture. Similarly, a snap-fit connection may be used in which the mating end of the impression coping device comprises a lip that fits over the mating surface of the dental fixture, forming a removable or releasable communication between the two. A fastener (e.g., a screw) can be used for seating the coping device properly.

In one embodiment, the impression coping device of the invention is attached by a radial friction fit formed between the castellated end with three axially-extending, radially resilient fingers and the corresponding hexagonal mating end of the dental fixture. The three fingers provide for an easy visual determination of whether the coping device is properly engaged or seated with the dental fixture. The fingers of the castellated end expand as the device is forced over the male hexagonal interface of the fixture. The radial friction fit prevents the coping device from rotating on the fixture. Similarly, a snap-fit connection may be used in which the mating end of the impression coping device comprises a lip that fits over the mating surface of the dental fixture, forming a removable or releasable connection between the two. Such a device is not clamped to a fixture, but is seated on the flats or "points" on the mating hex on the fixture, thereby providing a mating fit with resistance to rotation, but not requiring a clamping force.

The spaced-apart fingers provide for easy visual determination of whether the coping device is properly engaged or seated with the dental fixture. The spacing between fingers can be any distance that allows for visual inspection of the coping device as attached to the fixture. A preferred spacing of the fingers is between 0.5 mm and 3 mm. A particularly preferred spacing is between 1 mm and 2 mm. Alternatively, a castellated end with two axially-extending, radially resilient fingers, also is useful for visual determination of proper engagement or seating in either a friction-fit or snap-fit configuration. A fastener (e.g., a screw) can be used for seating the coping device properly.

To the extent that an impression coping is used that either relies upon a screw for seating the coping on the dental fixture or uses a screw to further secure and seat a coping (in a supplementary manner) on the dental fixture (once the coping has been seated using modes such as a radial friction fit or snap-fit, described above), screws having two or more threaded areas are provided according to the invention such that a single screw can mount to variously sized threaded bores in various dental fixtures. FIG. 7B shows a screw 116 inserted through an impression coping 110. This embodiment of an impression coping, while not having a castellated head, has a female, hexagonal mating surface 120 (FIG. 7A) for releasable mating with a male, hexagonal interface on a dental fixture. Such mating can take place, for example, but without limitation, as a friction fit or a snap-fit. A screw can further secure and seat the coping. Three sizes of impression copings 110, 112, 114 are shown attached to a platform 100 in FIG. 7. These impression copings 110, 112, 114 have with female, hexagonal mating surfaces 120 that can operate in a similar fashion to copings with a castellated head as described above. For example, the female, hexagonal mating surfaces 120 of the impression copings 110, 112, 114 can range in size from about 2 mm to about 4 mm, as measured from flat to flat. The impression copings 110 can have an overall length from about 10 mm to about 20 mm. These dimensions are exemplary and not meant to be limiting.

Flanges 132 are located towards the proximal end of the impression copings 110, 112, 114 which is the end of the impression copings 110, 112, 114 opposite from the female, hexagonal mating surfaces 120. The flanges 132 are oriented radially about the central axis of the impression copings 110, 112, 114. The flanges 132 smoothly flare outward as they proceed away from the proximal end (towards the female, hexagonal mating surface 120) of the impression copings 110, 112, 114. These flared flanges 132 extend beyond (e.g., length DDDD) the radius of the outer diameter of the impression copings 110, 112, 114 as measured from the central axis of the impression copings 110, 112, 114 to the outer surface of the impression copings 110, 112, 114 where the flanges 132 extend to their furthest point. At this point, the flanges 132 extend beyond the radius by a length in an amount of about 5% to about 100% or more of the radius at that point (e.g., length DDDD). Some second flanges 133 also smoothly flare outward as they proceed from the proximal end of the impression copings 110, 112, 114, but the flared portion ends prior to the point at which the flared portion of the other flanges 132 ends. As such, the second flanges 133 have a blunt face compared with the smooth taper of the other flanges 132. The second flanges 133 also are radially arranged about the central axis of the impression copings 110, 112, 114, and are located towards the proximal end of the impression 10 copings 110, 112, 114, which is the end of the impression copings 110, 112, 114 opposite from the female, hexagonal mating surfaces 120. The two types of flange 132, 133 embed in impression material when an impression is taken. The location of their most outwardly extending portions (e.g., as seen at the outward most position along length DDDD) along the length of the impression copings 110, 112, 114 can provide an anchor for impression material that is more towards the interior of a mass of the impression material when in use than would be flanges that are located at an extreme end of an impression coping.

Figure 10A:
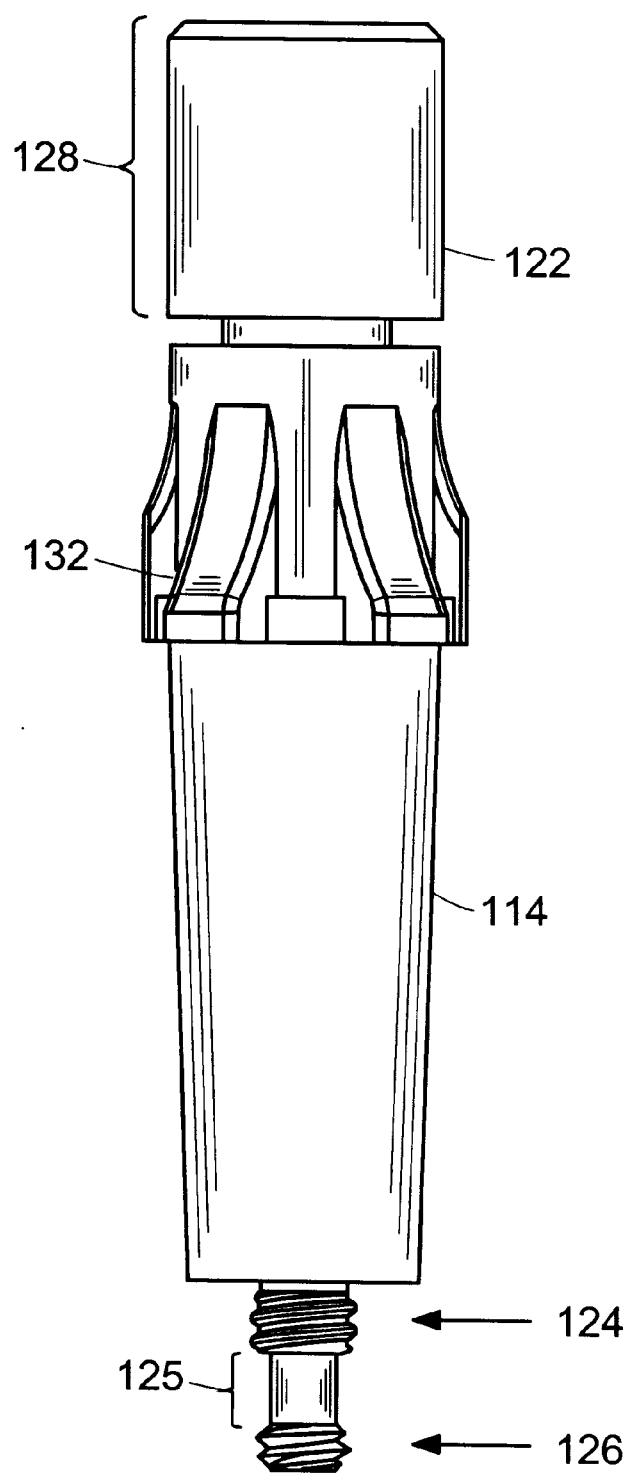
FIG. 10A depicts a screw with two threaded portions inserted through a first impression coping of FIG. 7A.
Figure 10B:
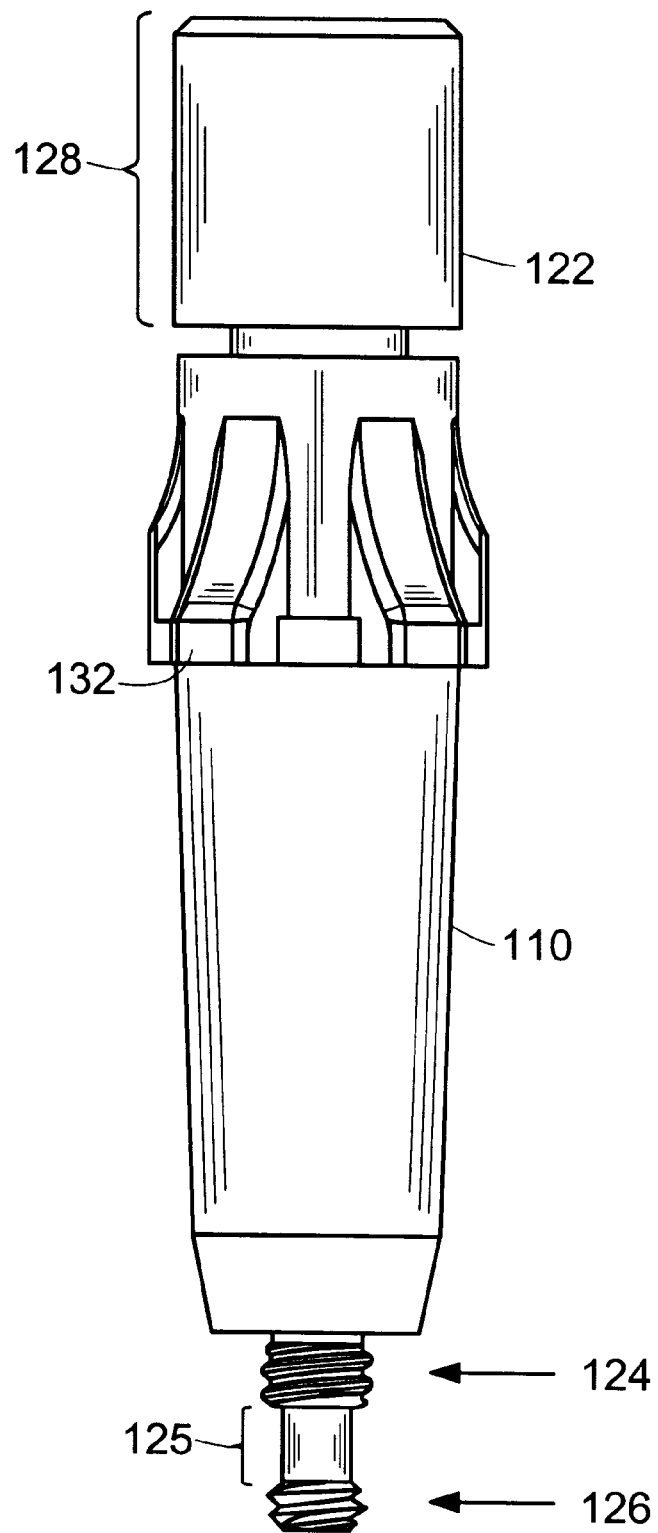
FIG. 10B depicts the screw of FIG. 10A inserted through a second impression coping of FIG. 7A.

Now referring to FIG. 10A, a screw 122 having a knurled top section 128 and having two threaded portions 124, 126 can be inserted through an impression coping 114, such as one that is shown attached to a platform 100 in FIG. 7A. A top threaded portion 124 is located towards the proximal end (i.e., the end of the screw 122 that faces the dental professional during placement of the screw 122) of the screw 122 and a bottom threaded portion 126 is located towards the distal end (i.e., the end of the screw 122 that faces away from the dental professional during placement of the screw 122) of the screw 122. Throughout the specification, except as otherwise indicated, when referring to a screw, distal refers to the end of a screw that faces away from a dental professional when placing the screw and proximal refers to that end of the screw that faces towards a dental professional when placing the screw. The major diameter of the bottom threaded portion 126 of the screw 122 is smaller than the major diameter of the top threaded portion 124 of the screw 122. A non-threaded portion 125 of the screw 122 is disposed between the top threaded portion 124 and the bottom threaded portion 126 of the screw 122. Either of the two threaded portions 124, 126 of the screw 122 can engage with complementary threads that are similarly sized in a bore in a dental fixture. Thus, any dental fixture with one of two differently sized threaded bores can be engaged with the screw 122. For example, but without limitation, LifeCore of Chaska, Minnesota manufactures a line of dental fixtures having one of two differently sized threaded bores. Such a screw could be used with these fixtures. In FIG. 10B, the same screw 122 is shown inserted through a second impression coping 110; the impression coping 110 is shown attached to a platform 100 in FIG. 7A.

Various embodiments of dual-threaded-section screws can have any of a variety of dimensions. For example, FIGS. 10C–10F provide a more detailed description of the screw shown in FIG. 10A. This example of a screw of the invention is exemplary and is not meant to be limiting. The screw 122 is meant to be clean and free of burrs, all sharp edges are broken 0.05 mm, and the chamfer of all threads is 45 degrees on both ends. FIG. 10C shows a top view of the screw 122 such that the proximal most end of the screw 122 is visible. The screw 122 has a hollow bore 134 that extends through the central axis of the screw 122. At least the most proximal portion of this bore has a hexagonal shape. In this example, the bore is a 1.27 mm hex D that is a minimum of 2 mm deep. A wrench can be inserted into the bore 134 so that a dental professional can tighten the screw 122 in addition to in, or instead of, finger tightening the screw 122 with the top knurled section 128. The top knurled section 128 has a medium knurl as a grip surface (FIG. 10F).

FIG. 10D shows a profile of the screw 122 taken as a section along line B—B which is taken along the central axis of the screw 122. The top threaded portion 124 of the screw 122 is a standard thread defined as M2.5×0.45 4 g. One skilled in the art is able to create the appropriate thread based on this definition. The bottom threaded portion 126 of the screw 122, encircled by circle A, has a custom thread design shown in more detail in FIG. 10E. Generally, the major diameter E of the bottom threaded portion 126 of the screw 122 is about 1.80 mm (for example, but without limitation, the diameter can be about 0.02 mm larger or 0.03 smaller than the given diameter); the minor diameter F is about 1.48 mm (for example, but without limitation, the diameter can be about 0.05 mm smaller than the given diameter); the pitch G is about 0.35 threads per mm (which is the equivalent of about 72 to about 73 threads per inch); the angle H of a side of the thread in cross-section relative to the minor diameter F is about 60 degrees; and the roots and crests of the thread are slightly flattened such that at least one of the crests I has a flat surface that is 0.02 mm in length. The screw 122 also has a shoulder 130. Typically, a screw 122 is constructed from a metal such as stainless steel or titanium.

The shoulder 130, coincidentally, is located at a datum point J for describing the length of the screw 122 portions. The diameter T of the screw 122 at the datum point J is about 3.00 mm. The center point K of a bulge is located about 1.00 mm proximal from the datum point J. The bulge, at point L, has a radius of curvature of about 1.00 mm and, at the center point K, has a diameter of about 3.10 mm. A shoulder forming the distal most end of the knurled top section 128 is located at point M, which is about 4.00 mm proximal from the datum point J. The section between the proximal end of the bulge and point M is generally cylindrical and has a diameter of about 2.85 mm at point N. The proximal most point P of the screw 122 is located about 9.00 mm from the datum point J. About a 45 degree chamfer Q (the angle of all chamfers shown in the screw 122) begins at point P and ends at point R, which is about 8.70 mm from the datum point J. The diameter S of the screw 122 at point R is about 4.70 mm. Distal to the datum point J the screw 122 has a generally cylindrical shape over a portion of screw 122, and, at point U, the screw 122 has a diameter (which is the general diameter of this portion of the screw 122) of about 2.40 mm. Distal to point U, the screw 122 narrows to another cylindrical section, and, at point V, the screw has a diameter of about 1.85 mm (which is the general diameter of this portion of the screw 122). The screw 122 transitions between the two diameters U, V between points CC (about 7.75 mm from the datum point J) and DD (about 8.00 mm from the datum point J). Distal to point V, and within the top threaded portion 124 of the screw 122, the diameter of the top threaded portion is about 2.4 mm at point Y, due to knocking down the edges of the M2.5×0.45 4 g screw threads. The screw 122 transitions between the section having a diameter corresponding with point V and the top threaded portion 124 at a chamfer beginning point EE which is about 9.8 mm from the datum point J. The portion 125 of the screw 122 between the two threaded portions 124, 126 is unthreaded, has a generally cylindrical shape, and has a diameter of about 1.45 mm at point Z. This diameter is also found at point FF, distal to the bottom threaded portion 126 of the screw 122. The top threaded portion 124 of the screw 122 transitions to the section having a diameter corresponding with point Z at a chamfer located at point GG, which is about 11.30 mm distal from the datum point J. The portions of the screw 122 having the diameter of point Z, FF transition to the bottom threaded portion 126 at points HH and JJ, which are about 13.40 mm and about 14.40 mm, respectively, distal from the datum point J. At point KK, which is about 14.70 mm from the datum point J, the screw 122 is chamfered to the distal end LL of the screw 122, which is about 14.90 mm from the datum point J.

Figure 11A:
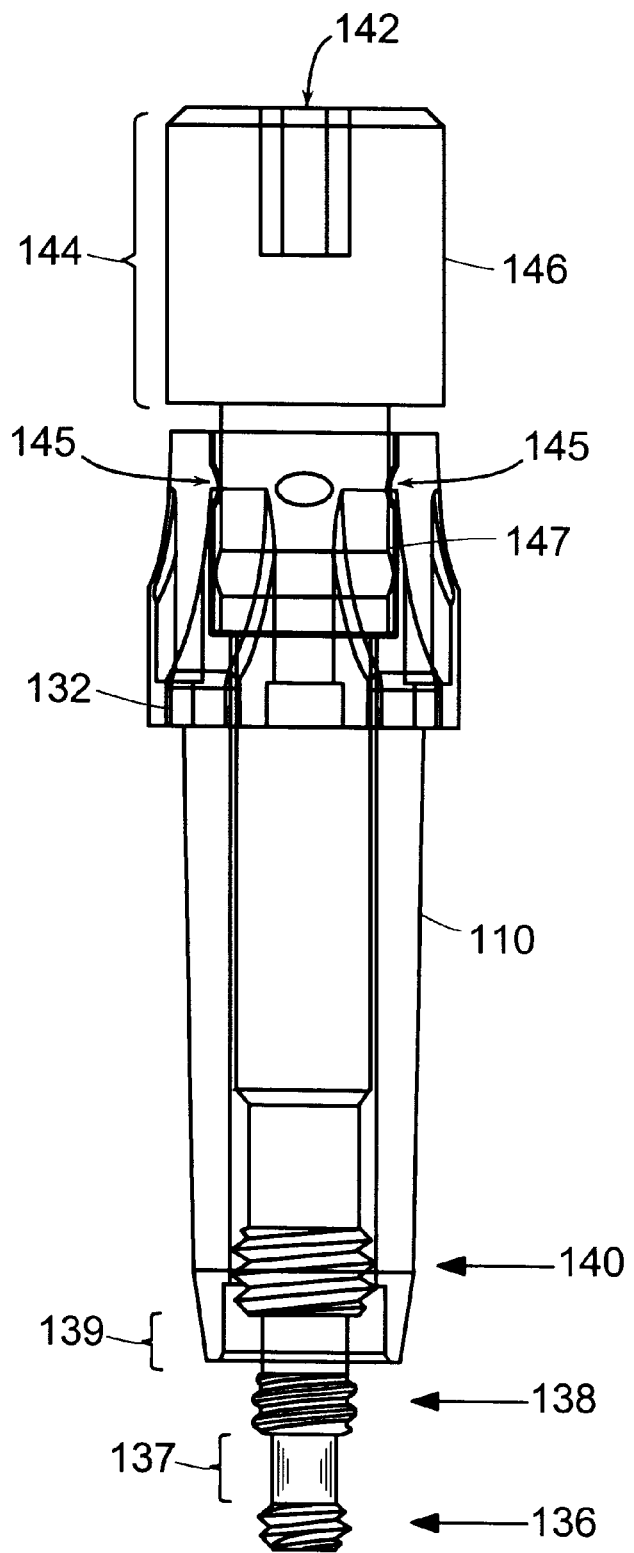
FIG. 11A depicts a section view of a screw with three threaded portions inserted through a second impression coping of FIG. 7A.
Figure 11B:
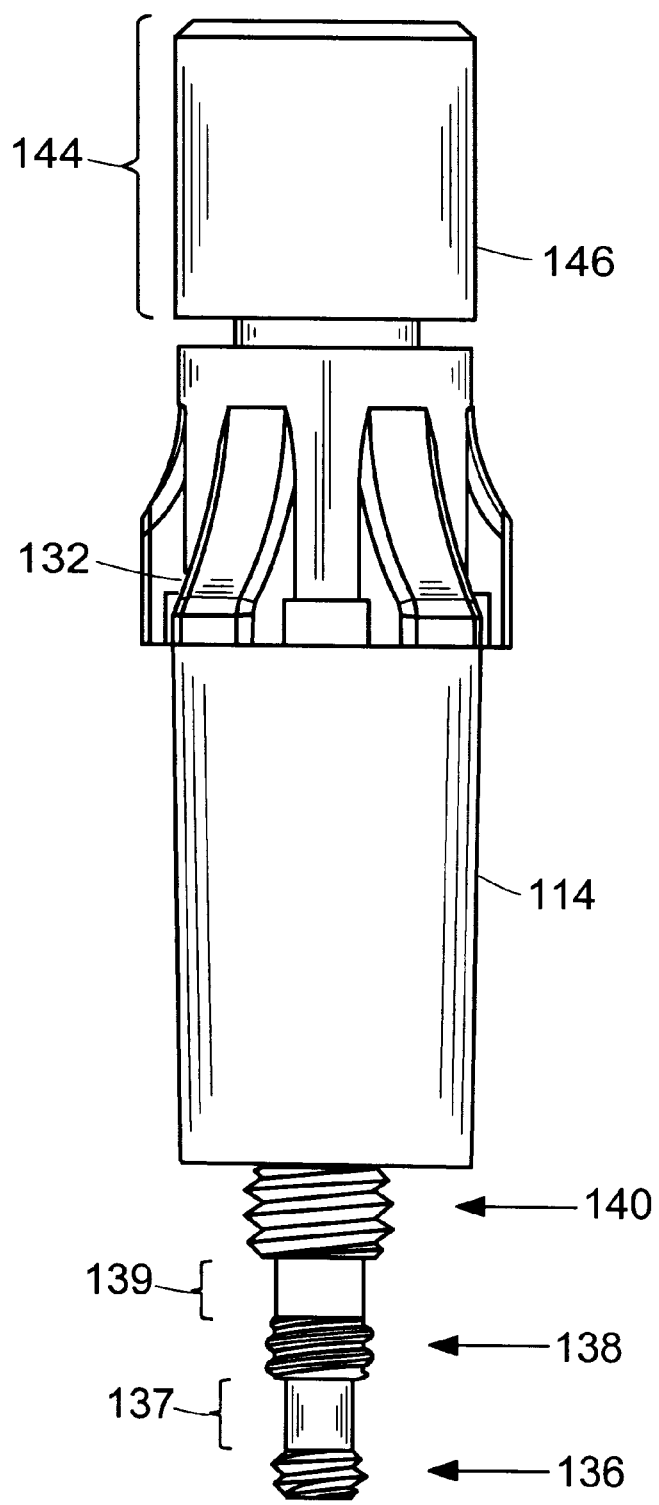
FIG. 11B depicts the screw of FIG. 11A inserted through a first impression coping of FIG. 7A.

Referring to FIG. 11A, another embodiment of a screw 146 has a knurled top section 144 and three threaded portions 136, 138, 140. The screw 146 can be inserted through an impression coping 110, such as one that is shown attached to a platform 100 in FIG. 7A. A top threaded portion 140 is located towards the proximal end of the screw 146 and a bottom threaded portion 136 is located towards the distal end of the screw 146. A middle threaded portion 138 is located between the top threaded portion 140 and the bottom threaded portion 136. The major diameter of the bottom threaded portion 136 of the screw 146 is smaller than the major diameter of the middle threaded portion 138 of the screw 146 which is smaller than the major diameter of the top threaded portion 140 of the screw 146. A first non-threaded portion 139 of the screw 146 is disposed between the top threaded portion 140 and the middle threaded portion 138 of the screw 146, and a second non-threaded portion 137 of the screw 146 is disposed between the middle threaded portion 138 and the bottom threaded portion 136 of the screw 146. Any of the three threaded portions 136, 138, 140 of the screw 146 can engage with complementary threads that are similarly sized in a bore in a dental fixture. Thus, any dental fixture with one of three differently sized threaded bores can be engaged with the screw 146. For example, Noble BioCare of Yorba Linda, California manufactures a line of dental fixtures having one of three differently sized threaded bores. In FIG. 11B, the same screw 146 is shown inserted through a second impression coping 114; the impression coping 114 is shown attached to a platform 100 in FIG. 7A.

Figure 11D:
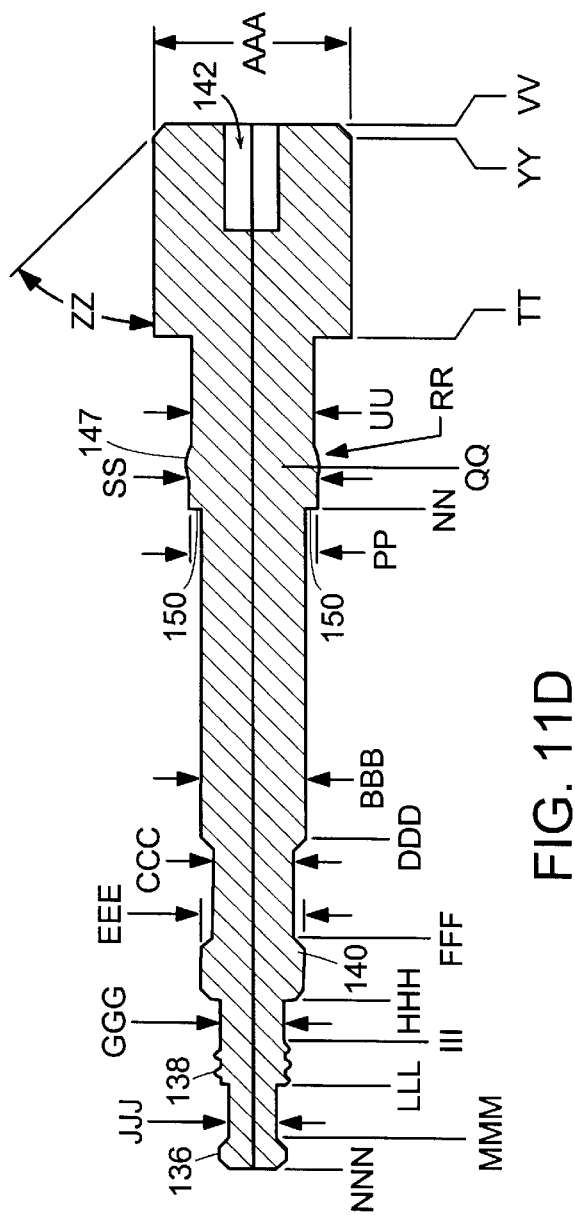
FIG. 11D depicts a sectioned, stylized profile view of the screw of FIG. 11A taken along line C—C of FIG. 11C.
Figure 11C:
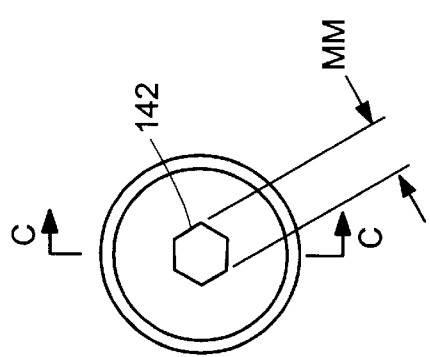
FIG. 11C depicts a top view of the screw of FIG. 11A.
Figure 11E:
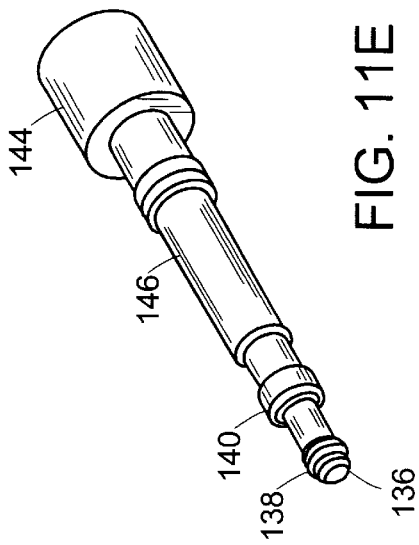
FIG. 11E depicts a highly stylized view of the screw of FIG. 11A.

Various embodiments of triple-threaded-section screws can have any of a variety of dimensions. For example, FIGS. 11C–11E provide a more detailed description of the screw shown in FIG. 1A. This example is exemplary and is not meant to be limiting. The screw 146 is meant to be clean and free of burrs, all sharp edges are broken 0.05 mm, and the chamfer of all threads is 45 degrees on both ends. FIG. 11C shows a top view of the screw 146 such that the proximal most end of the screw 146 is visible. The screw 146 has a hollow bore 142 that extends through the central axis of the screw 146. At least the most proximal portion of this bore has a hexagonal shape. In this example, the bore is a 1.27 mm hex MM that is a minimum of 2 mm deep. A wrench can be inserted into the bore 142 so that a dental professional can tighten the screw 146 in addition to in, or instead of, finger tightening the screw 146 with the top knurled section 144. The top knurled section 144 has a medium knurl as a grip surface (FIG. 11E).

FIG. 11D shows a profile of the screw 146 taken as a section along line C—C which is taken along the axis of the screw 146. The top threaded portion 140 of the screw 146 is a standard thread defined as M2.5×0.45 4 g; the middle threaded portion 138 of the screw 146 is a standard thread defined as M2.0×0.40 4 g; and the bottom threaded portion 136 of the screw 146 is a standard thread defined as M1.6×0.35 4 g. One skilled in the art is able to create the appropriate threads based on these definitions. The screw 146 also has a shoulder 150. Typically, a screw 146 is constructed from a metal such as stainless steel or titanium.

The shoulder 150, coincidentally, is located at a datum point NN for describing the length of the screw 146 portions. The diameter PP of the screw 146 at the datum point NN is about 3.00 mm. The center point QQ of a bulge 147 is located about 1.00 mm proximal from the datum point NN. The bulge 147 has a radius of curvature of about 1.00 mm at point RR and has a diameter SS of about 3.10 mm at the center point QQ of the bulge 147. A shoulder forming the distal most end of the knurled top section 144 is located at point TT, which is about 4.00 mm proximal from the datum point NN. The section between the proximal end of the bulge 147 and point TT is generally cylindrical and has a diameter of about 2.85 mm at point UU. The proximal most point VV of the screw 146 is located about 9.00 mm from the datum point NN. About a 45 degree chamfer ZZ (the angle of all chamfers shown in the screw 146) begins at point VV and ends at point YY, which is about 8.70 mm proximal from the datum point NN. The diameter AAA of the screw 146 at point YY is about 4.70 mm. Distal to the datum point NN the screw 146 has a generally cylindrical shape over a portion of screw 146, and, at point BBB, the screw 146 has a diameter (which is the general diameter of this portion of the screw 146) of about 2.40 mm. Distal to point BBB, the screw 146 narrows to another cylindrical section, and, at point CCC, the screw 146 has a diameter of about 1.85 mm (which is the general diameter of this portion of the screw 146). The screw 146 transitions between the two diameters BBB, CCC starting at point DDD (about 7.75 mm from the datum point NN). Distal to point CCC, and within the top threaded portion 140 of the screw 146, the diameter EEE of the top threaded portion 140 of the screw 146 is about 2.4 mm, due to knocking down the edges of the M2.5×0.45 4 g screw threads. The screw 146 transitions between the section having the diameter corresponding with point CCC and the top threaded portion 140 at a chamfer beginning at point FFF which is about 10.10 mm from the datum point NN. The portion 139 of the screw 146 between the top threaded portion 140 and the middle threaded portion 138 is unthreaded, has a generally cylindrical shape, and has a diameter of about 1.45 mm at point GGG. The top threaded portion 140 of the screw 146 transitions to the portion 139 of the screw 146 having the diameter corresponding with point GGG at a chamfer located at point HHH, which is about 11.60 mm from the datum point NN. The portion 139 of the screw 146 having the diameter of point GGG transitions to the middle threaded portion 138 at point III which is about 12.60 mm from the datum point NN. Distal to the middle threaded portion 138 is a portion 137 of the screw 146 that is unthreaded, has a generally cylindrical shape, and has a diameter of about 1.10 mm at point JJJ. The middle threaded portion 138 transitions to the portion 137 of the screw 146 having the diameter of point JJJ at point LLL, which is about 13.60 mm from the datum point NN. The portion 137 of the screw 146 having the diameter of point JJJ, distal to that point, transitions to the bottom threaded portion 136 at point MMM, which is about 14.85 mm from the datum point NN. The distal end NNN of the screw 146, which is about 15.60 mm from the datum point NN, is chamfered.

Each of the two screw embodiments 122, 146 described above have a bulge (with center points K and QQ, respectively). This feature can be used in combination with an impression coping that has a lip (e.g., the lip 145 shown in FIG. 11A) to "lock" a screw to an impression coping. Any screw, not just these two screws, can include a similar bulge and can "lock" in a similar manner. A dental professional might prefer the two components to be locked together when he is seating the impression coping on the dental fixture to minimize the risk that either component will accidentally be dropped into the patient's mouth or onto the non-sterile floor of the room in which the procedure is taking place, as well as minimize the risk that the seated impression coping will become dislodged while the screw is being used to optimally seat the impression coping. Generally, and referring to FIGS. 11A and 11D, the bulge 147 has a slightly larger outer diameter (e.g., 3.10 mm) than the inner diameter of the lip 145 (e.g., 3.00 mm) located on the inside wall of the hollow impression coping 110, but the bulge 147 fits within the inner diameter of the impression coping 110 which is larger than the outer diameter of the bulge 147 (e.g., the inner diameter of the impression coping 110 can be at least about 0.16 mm larger than the inner diameter of the lip 145 in the general area of the lip 145). This configuration creates a situation where the bulge 147 and the lip 145 can interact with a radial interference interaction. The dimensions given above are exemplary and not meant to be limiting. The dental professional inserts the screw 146 through the impression coping 110 at the end having the flanges 132 (the proximal end of the impression coping 110) and forces the bulge 147 distally (towards the end of the impression coping 110 without the flanges 132) past the lip 145 of the impression coping 110, "locking" the two components together. The impression coping 110 then is seated on the dental fixture and the screw 146 is tightened into the bore of the dental fixture. After an impression of the local dentition is made, as described below, the screw 146 is unscrewed. The force of unscrewing the screw 146 forces the bulge 147 of the screw 146 proximally (towards the end having the flanges 132) past the lip 145 of the impression coping 110, separating the two components so that the impression coping and the cured impression material can be removed.

Moreover, the impression copings themselves can be designed to operate in combination with screws with multiple threaded portions. Generally, when a screw with multiple threaded portions is inserted through the impression coping, the length of the coping can be designed to expose the particular threaded portion of the screw that is correctly sized for mating with the particular sized bore of the dental fixture. For example, in a range of sizes of impression copings, an impression coping with the smallest female hexagonal mating surface (of a range of female hexagonal mating surface sizes designed to match the various male hexagonal interface sizes of a particular manufacturer's line of dental fixtures) has the longest length (e.g., impression coping 110 of FIG. 7A), and the impression coping with the largest female hexagonal mating surface (of the range of female hexagonal mating surface sizes designed to match the various male hexagonal interface sizes of a particular manufacturer's line of dental fixtures) has the shortest length (e.g., impression coping 114 of FIG. 7A). In many dental fixtures, a small sized male, hexagonal interface corresponds with a small sized threaded bore in the dental fixture. The impression coping having a small complementary female, hexagonal mating surface and a longer length enables the coping to be fully seated on the smallest dental fixture (with the smallest bore), because a more distally located threaded portion of the screw (with the matching, smaller thread size) can engage with the dental fixture before a more proximally located threaded portion on the screw (with a non-matching, larger thread size) comes into contact with the top of the dental fixture, preventing optimal seating of the impression coping.

After the impression coping device is attached to the dental fixture, however that is accomplished, an impression of the local dentition is made. An elastomeric impression material, such as, for example, polyether siloxane or polyvinyl siloxane, is pressed onto the coping device and surrounding teeth. The impression preferably is made without contacting the gum tissue. The impression is allowed to harden for approximately one minute before removal. Once the impression is formed, the impression coping device, and attached impression material, are removed by pulling the coping away from the dental implant fixture. If a screw has been used to seat the coping, the screw must be unscrewed to remove the coping. The coping and the impression are removed simultaneously. After the impression is made, the gingival tissue is replaced over the bone and around the implanted dental fixture to promote healing. Healing generally occurs within about 4 to about 9 months.

Because dental fixtures are made in various sizes, impression copings are also made in a variety of sizes to allow mating between the two. During a dental procedure, patient discomfort is minimized if the procedure's length is shortened. Also, the dental professional is better able to prepare for a dental procedure if the tools for that procedure are organized and easily sterilizable. Accordingly, and referring to FIGS. 6 and 7A, a platform 100 is provided to hold and organize variously-sized impression copings 110, 112, 114. In one embodiment of the platform, the impression copings 110, 112, 114 are attached to the platform 100 at three positions 102, 104, 106. These impression copings 110, 112, 114 are exemplary, and not meant to be limiting, such that any of a variety of impression copings can be attached to the platform 100. Alternatively, the impression copings attached to the platform can have other distinguishing properties, besides size. For example, various embodiments of impression copings can be attached to the platform so that a dental professional can choose the desired impression coping configuration based on such criteria as the manufacturer of a dental fixture or personal preference.

In this embodiment, the platform 100 has a radius of curvature of about 6.63 mm, about 5.00 mm, about 60.00 mm, about 21.00 mm, about 6.00 mm, and about 6.63 mm at points PPP, QQQ, RRR, UUU, VVV, and YYY, respectively. The platform 100 also has a width ZZZ of about 48.00 mm, at the widest portion of the platform 100, and has a length AAAA of about 21.66 mm, at its longest as measured from the intersection of an attachment point 102, 104, 106 and the body of the platform 100. The platform 100 is about 1.00 mm thick. These dimensions may vary, and any dimensions given for the platform 100 are exemplary, and not meant to be limiting.

The platform 100 optionally is connected with a reinforcing member 108. The reinforcing member 108 can be inserted into the impression material before it has hardened if the dental professional is taking an impression of a relatively large area of the patient's mouth, such as when two or more dental fixtures have been implanted into the patient. The reinforcing member 108 can be used to stiffen the impression material, once it has cured, to avoid any deflection of the impression cast during later procedures. As such, a more accurate transfer of the impression is maintained throughout further steps in producing a dental abutment. Typically, the reinforcing member 108 is inserted into the impression material such that the main body of the reinforcing member 108 is at least partially embedded in the impression material and that a protrusion 111 protrudes from the impression compound. A dental professional can use this protrusion 11, for example, to gauge the depth to which the reinforcing member 108 has been inserted into the impression compound and/or to handle the impression cast once the impression material has cured. The protrusion 111 can have a radius of curvature of about 7.10 mm at point WWW, and the platform 100 and protrusion 111, while connected together, can have a length BBBB of about 30.66 mm. These dimensions are exemplary and are not meant to be limiting. The reinforcing member 108 has a more sharply curved portion 107 and a more shallowly curved portion 105 to generally match the shape of a patient's jaw. These portions 105, 107, as marked in the Figure, generally describe the location of the arcuate portions, but the markings can be altered from the present marking scheme in other embodiments while still maintaining a more sharply curved portion and a more shallowly curved portion. The reinforcing member 108 has a radius of curvature of about 63.50 mm and about 24.50 mm at points SSS and TTT, respectively. These dimensions are exemplary and are not meant to be limiting. Also, the reinforcing member 108 follows the same general contour as the platform 100, which has a more sharply curved section and a more shallowly curved section, as described above. The contour of the reinforcing member 108 also is similar to the contour of the layout of teeth in a mouth. The reinforcing member 108 also can be constructed in various sizes to accommodate variously sized mouths, such as the difference between an adult's mouth and a child's mouth. Furthermore, the reinforcing member 108 can be constructed with frangible points 103, 111. A dental professional can break off sections of the reinforcing member 108 at the frangible points 103, 111 in order to create a proper size or curvature of the reinforcing member 108 for inserting into impression material in the patient's mouth, depending upon the situation.

The platform 100, impression copings 110, 112, 114, and/or the reinforcing member 108 can be made from the same material. Plastics such as polycarbonate, high-impact polystyrene, or polyetherimide can be used, as well as other thermoformable or machineable materials. Also, a nylon (50% by weight)/bismuth subcarbonate (40% by weight)/fiberglass (10% by weight) material can be used and also is radiopaque, allowing parts to be visualized under an x-ray. The assembly of the platform 100, the impression copings 110, 112, 114, and/or the reinforcing member 108 can be produced by injection-molding techniques. Such production results in the impression copings 110, 112, 114 and reinforcing member 108 being frangibly attached to the platform 100. For example, the impression copings 110, 112, 114 and the reinforcing member 108 are attached to the platform at frangible connection points 102, 104, 106, 115, 117. When a dental professional wishes to use any of the components 108, 110, 112, 114, he will break off that component from the platform 100 at the frangible connection points 102, 104, 106, 115, 117. The platform, reinforcer, and/or impression copings alternatively can be formed from a metal, such as stainless steel or titanium.

Figure 8:
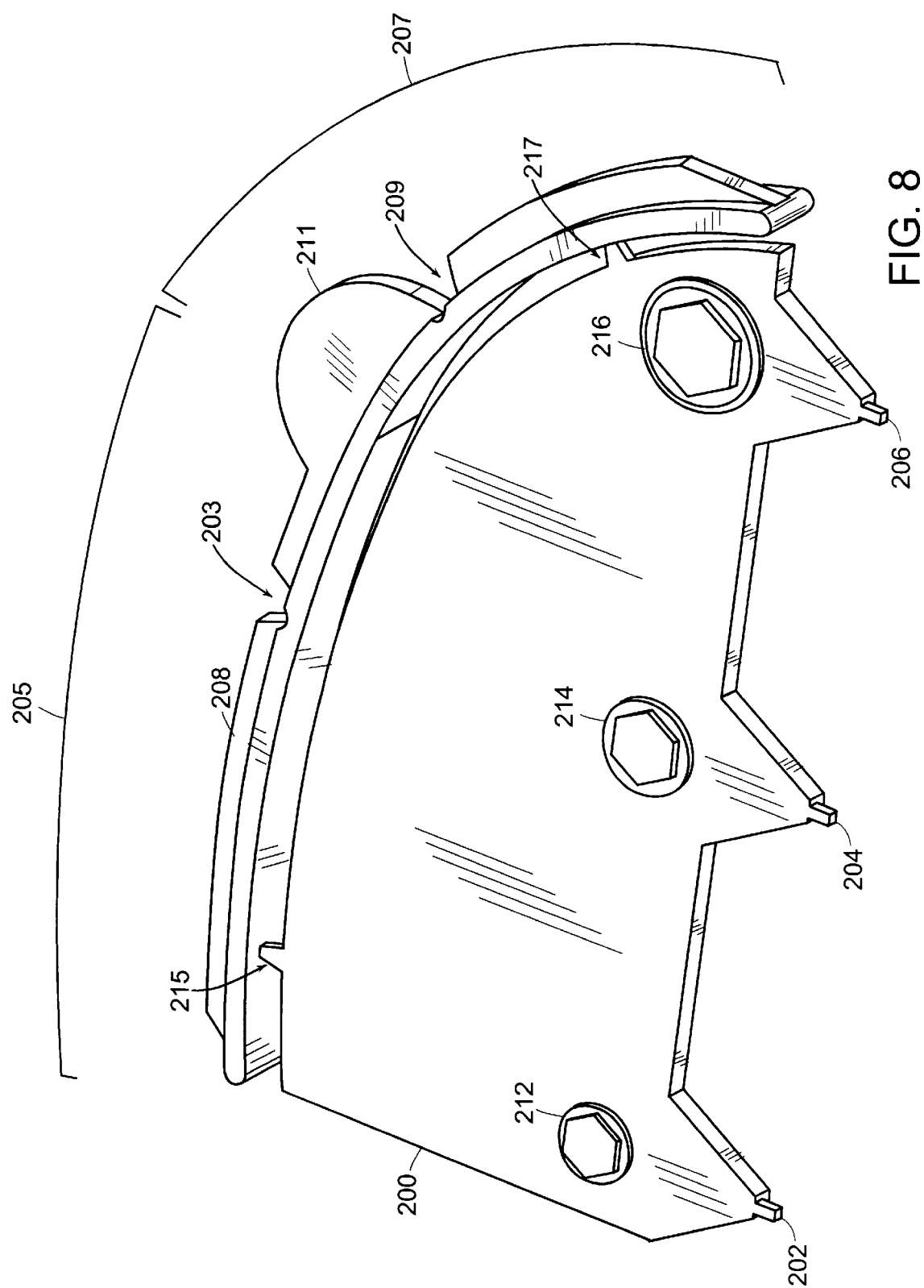
FIG. 8 depicts another embodiment of a platform attached to a reinforcing member.

A platform can take on many shapes and sizes. For example, FIG. 8 shows a platform 200 having a perimeter with sharp angles rather than the more arcuate perimeter of the platform 100 shown in FIGS. 6 and 7A. Additionally, three sizes of hexagonal heads 212, 214, 216 (small, medium, and large, for example) are molded into or affixed onto the platform 200. These hexagonal heads 212, 214, 216 are male and mate with the female hexagonal mating surface of certain impression copings. The hexagonal heads 212, 214, 216 can serve as a visual cue to the dental professional as to which sized impression coping is attached at each attachment point 202, 204, 206. Alternatively, other visual cues can be used in addition to, or in place of, the hexagonal heads 212, 214, 216, such as labeling with alphanumeric characters. Also, the hexagonal heads 212, 214, 216 can serve a corroborative function. For example, if the hexagonal heads 212, 214, 216 are the same size as the male hexagonal surfaces on the manufacturer's line of dental fixtures being used, the impression copings are detached from the attachment points 202, 204, 206, and the dental professional is unable to distinguish one impression coping from another because they are detached, then the dental professional can place the female hexagonal mating surface of the impression copings over the various male hexagonal heads 212, 214, 216, to identify the size of the impression coping by identifying the male hexagonal head with which the impression coping optimally mates. The reinforcing member 208 of FIG. 8 also has a perimeter with sharp angles rather than the more arcuate perimeter of the reinforcing member 108 shown in FIGS. 6 and 7A. However, the reinforcing member 208 retains a more sharply curved portion 207 and a more shallowly curved portion 205 as well as a protrusion 211 and frangible points 203, 209 for shortening the length of, or altering the curvature of, the reinforcing member 208. The reinforcing member 208 is attached at frangible attachment points 215, 217 to the platform 200. In another embodiment, FIG. 9 shows a platform 300 that also has a sharply angular perimeter like the platform 200 of FIG. 8, but also the platform 300 has a generally rectangular shape.

Figure 6:
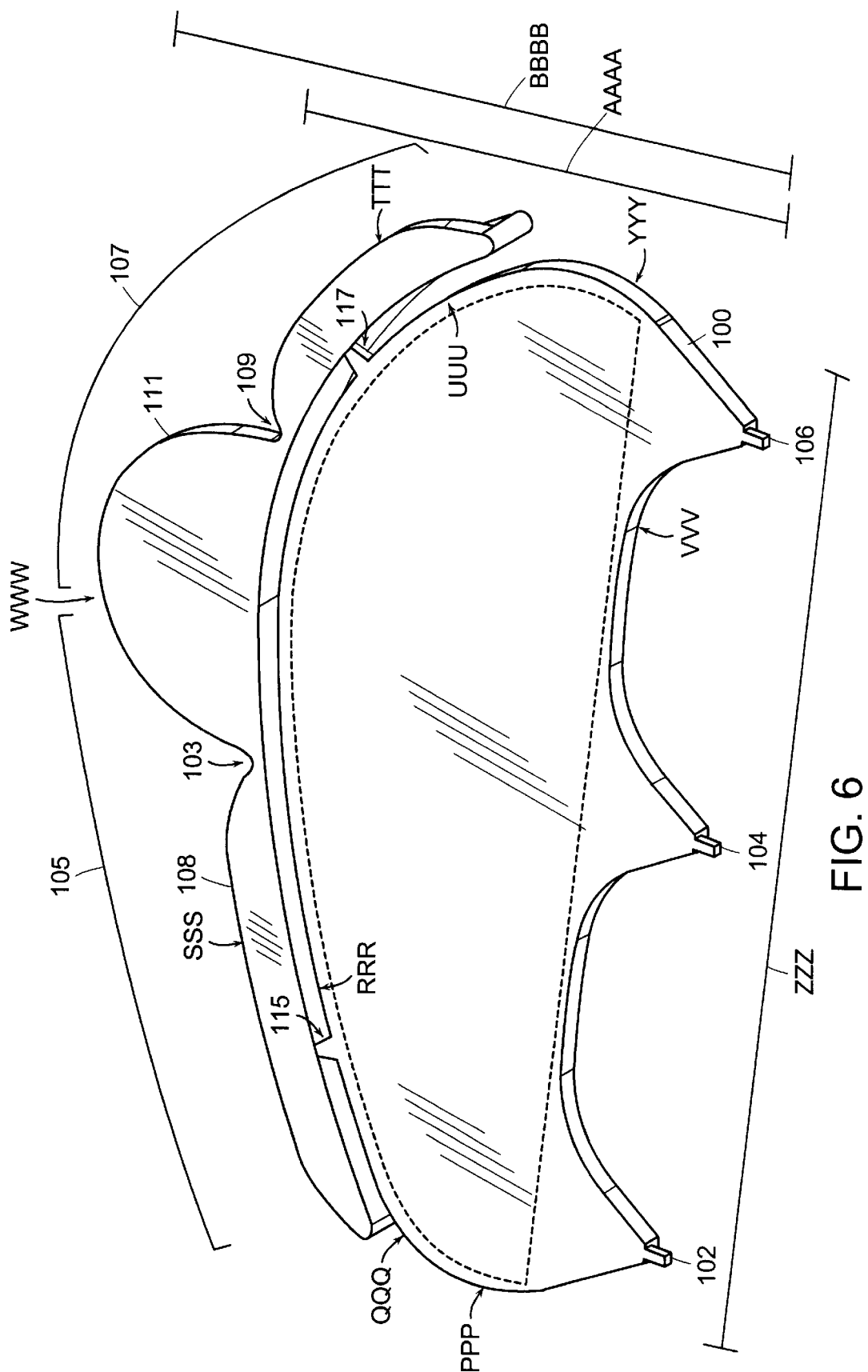
FIG. 6 depicts a platform attached to a reinforcing member.
Figure 9:
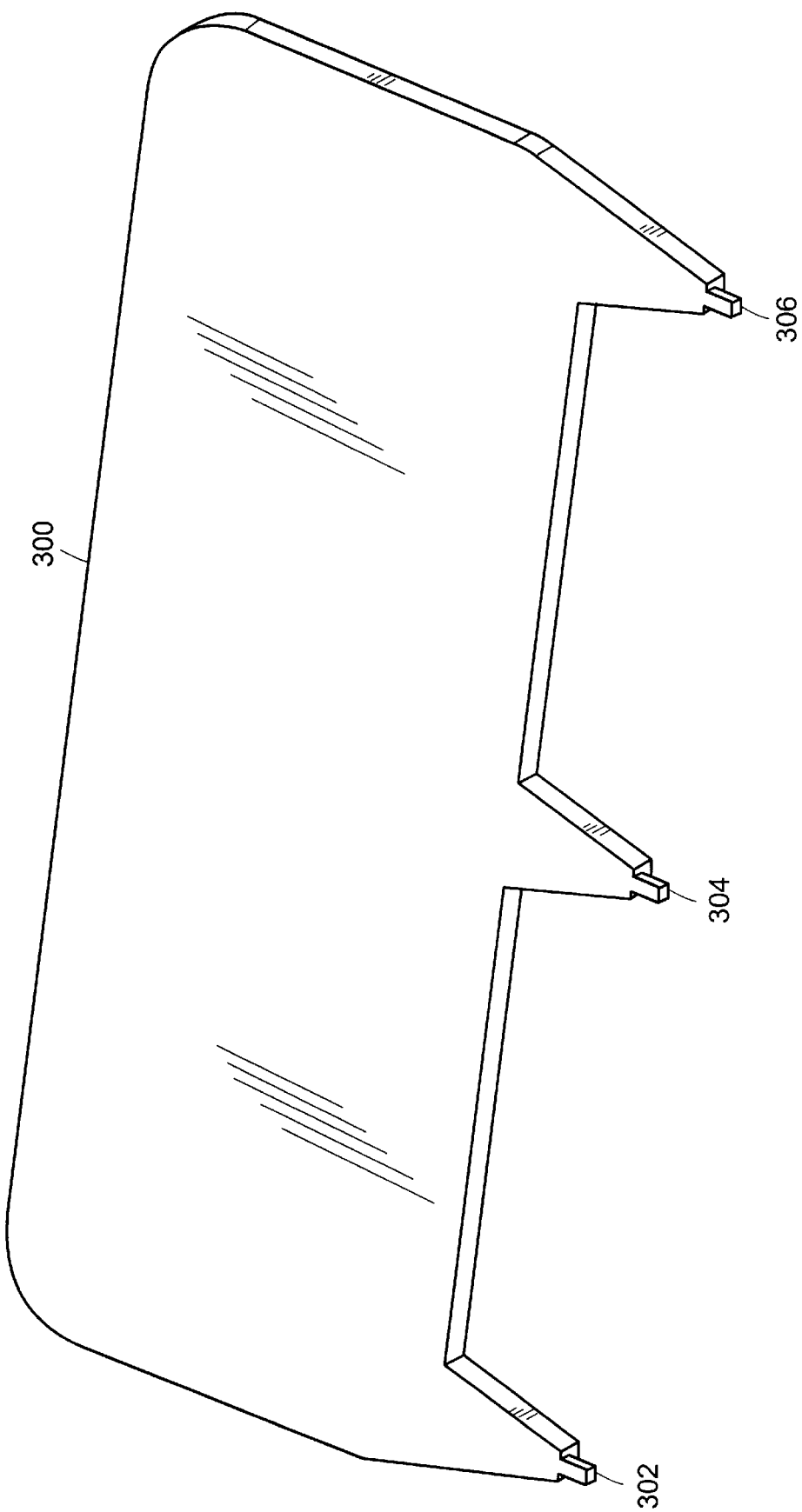
FIG. 9 depicts another embodiment of a platform.

Although three frangible attachment points 102, 104, 106, 202, 204, 206, 304, 306, 308 for impression copings are shown in FIGS. 6, 8 and 9 and two frangible attachment points 115, 117, 215, 217, for reinforcing members are shown in FIGS. 6 and 8, a platform can have any number of frangible attachment points for any number of impression copings, reinforcing members, or other dental tools. Also, greater or fewer frangible attachment points can be used for each component. Alternatively, the copings can be attached directly to a reinforcing member at frangible attachment points, without the need for a platform.

After the impression material cures and the impression coping(s) with hardened impression material is(are) removed, the impression coping device containing the attached impression material is attached to an analog fixture, which is then cast in a study cast previously made of the patient's mouth. The space surrounding the analog fixture is then filled and allowed to cure so that the analog fixture becomes part of the study cast. The rotational and positional alignment of the dental fixture is thus preserved with respect to the patient's natural dentition.

A pre-fabricated abutment, over which a crown is placed, is then constructed. A series of measurements are taken in order to guide the fabrication of an abutment and crown that closely approximate the tooth being replaced. Measurements are taken from all directions with respect to the angles of adjacent teeth and/or face construction. Measurements required to fabricate and position abutments for teeth are provided, for example, in Wheeler, *Dental Anatomy, Physiology and Occlusion* (5th ed. 1974), incorporated by reference herein. Measurements may be taken by several means including, but not limited to, a stent, a mold of the teeth, an optical device, or other measuring instrument. Using these measurements, an abutment is fabricated for insertion into the implanted dental fixture. Measurements may be made using a computerized abutment model, as disclosed in co-owned, co-pending U.S. patent application Ser. No. 08/372,323, incorporated by reference herein. The computer model is based on general abutment parameters for the particular tooth or teeth being replaced. Based upon the computer model, a wax model of the abutment is created on, for example, a Sanders Prototype, Inc. Model Maker 6 Pro® rapid prototyping machine. A crown that approximates the size and color of the patient's natural teeth is fabricated to fit over the abutment. A dental technician sculpts the crown with reference to the previously-prepared analog fixture and abutment. The crown is sculpted from, for example, wax or ceramic. The skilled artisan is aware that numerous methods may be used to fabricate an abutment and crown from an impression molding.

After the site of the implanted dental fixture in the patient's jawbone is healed, the abutment is screwed into place in the dental fixture. The crown is attached to the abutment with an adhesive and/or a lateral set screw.

The impression coping system of the invention makes it quicker and easier for a practitioner to prepare a crown and abutment, while preserving the exact rotational and positional alignment of the patient's natural dentition.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A fastener for use with an impression coping, the fastener comprising:
    a first threaded portion along an axis and having a first major diameter; and
    a second threaded portion along the axis and having a second, different major diameter, wherein the first threaded portion and the second threaded portion are separated by an unthreaded portion, wherein the first threaded portion and the second threaded portion are disposed at a distal portion of the fastener remote from a proximal end of the fastener, and wherein at least one other unthreaded portion is disposed between the distal portion and the proximal end.

2. The fastener of claim 1 further comprising a third threaded portion along the axis and separated from the second threaded portion by a second unthreaded portion.

3. The fastener of claim 2 wherein the third threaded portion has a major diameter of about 1 millimeter to about 3 millimeters.

4. The fastener of claim 2 wherein the second unthreaded portion comprises the at least one other unthreaded portion.

5. The fastener of claim 1 wherein the first major diameter is smaller than the second major diameter.

6. The fastener of claim 5 wherein the first threaded portion is located closer to a distal end of the fastener than the second threaded portion.

7. The fastener of claim 1 further comprising a bulge concentric with the axis at a location that is closer to the proximal end of the fastener than is the second threaded portion.

8. The fastener of claim 7 further comprising a shoulder concentric with the axis at a location that is closer to the distal end of the fastener than is the bulge.

9. The fastener of claim 1 wherein at least one of the first threaded portion and the second threaded portion has a major diameter of about 1 millimeter to about 3 millimeters.

10. The fastener of claim 9 wherein the first threaded portion has a major diameter of between about 1 millimeter to about 2 millimeters and the second threaded portion has a different major diameter of between about 1.5 millimeter to about 3 millimeters.

11. The fastener of claim 1 wherein at least one of the threaded portions is capable of engaging with a dental fixture.

12. A method of seating an impression coping, the method comprising the steps of:
    providing a fastener comprising a first threaded portion along an axis and having a first major diameter and a second threaded portion along the axis and having a second, different major diameter, wherein the first threaded portion and the second threaded portion are separated by an unthreaded portion, wherein the first threaded portion and the second threaded portion are disposed at a distal portion of the fastener remote from a proximal end of the fastener, and wherein at least one other unthreaded portion is disposed between the distal portion and the proximal end;
    inserting the fastener through an impression coping; and
    securing the fastener to a dental fixture.

13. A dental impression kit comprising:
    an impression coping; and
    a fastener for inserting through the impression coping to seat the impression coping on a dental fixture, the fastener comprising a first threaded portion along an axis and having a first major diameter and a second threaded portion along the axis and having a second, different major diameter, wherein the first threaded portion and the second threaded portion are separated by an unthreaded portion, wherein the first threaded portion and the second threaded portion are disposed at a distal portion of the fastener remote from a proximal end of the fastener, and wherein at least one other unthreaded portion is disposed between the distal portion and the proximal end.

14. The kit of claim 13 wherein the impression coping comprises a length that exposes a selected portion of the fastener when the fastener is inserted though the impression coping.

15. The kit of claim 13 wherein the fastener further comprises a bulge concentric with the axis and wherein an outer diameter of the bulge is larger than an inner diameter of a lip located within the impression coping.

16. The kit of claim 13 wherein the fastener and impression coping interact with a radial interference interaction.

* * * * *